United States Patent
Oliver et al.

(10) Patent No.: US 7,812,147 B2
(45) Date of Patent: Oct. 12, 2010

(54) STREPTOCOCCUS UBERIS ADHESION MOLECULE

(75) Inventors: Stephen P. Oliver, Maryville, TN (US); Raul A. Almeida, Knoxville, TN (US); Douglas A. Luther, Louisville, TN (US); Hee-Myung Park, Suwon-si (KR)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 12/384,268

(22) Filed: Apr. 2, 2009

(65) Prior Publication Data

US 2009/0226480 A1 Sep. 10, 2009

(51) Int. Cl.
C07H 21/04 (2006.01)
C07H 21/02 (2006.01)
A61K 39/02 (2006.01)
A61K 39/09 (2006.01)

(52) U.S. Cl. .................. 536/23.7; 536/24.32; 536/23.1; 424/234.1; 424/244.1

(58) Field of Classification Search ....................... None
See application file for complete search history.

(56) References Cited

FOREIGN PATENT DOCUMENTS

| EP | 1033405 A2 | 9/2000 |
|---|---|---|
| WO | WO 98/21231 | 5/1998 |
| WO | WO 01/75067 | 10/2001 |
| WO | WO 02/064766 | 8/2002 |

OTHER PUBLICATIONS

Fang, W, et al, "Effects of lactoferrin and milk on adherence of *Streptococcus uberis* to bovine mammary epithelial cells," Am J Vet Res, 61:275-279 (2000).
Fang, W, et, "Protein expression by *Streptococcus uberis* in co-culture with bovine mammary epithelial cells," FEMS Microbiology Letters, 166: 237-242 (1998).
Fang, W and Oliver, SP, "Identification of lactoferrin-binding proteins in bovine mastitis-causing *Streptococcus uberis*," FEMS Microbiology Letters, 176:91-96 (1999).
Gilbert, FB, et al, "Induction of surface-associated proteins of *Streptococcus uberis* by cultivation with extracellular . . . ," FEMS Microbiology Letters, 156:161-164 (1997).
Jiang, M, et al, "A bovine lactoferrin-binding protein of *Streptococcus uberis* . . . ," Abstract B-503, Proceedings of the Am Soc of Microbiology, 97th General Meeting (1997).
Park, HM, et al, "Binding of bovine lactoferrin to *Streptococcus dysgalactiae* subsp. *dysgalactiae* isolated from cows . . . ," FEMS Microbiology Letters, 208:35-39 (2002).
Park, HM, et al, "Identification of lactoferrin-binding proteins in *Streptococcus dysgalactiae* subsp. *dysgalactiae* and . . . ," FEMS Microbiology Letters, 207:87-90 (2002).
Rainard, P, "Binding of bovine lactoferrin to *Streptococcus agalactiae*," FEMS Microbiology Letters, 98:235-240 (1992).
Herbert, et al, The Dictionary of Immunology. Academic Press, 3rd Edition, London, pp. 58-59 (1985).
McGuiness, et al, Lancet, 337:514-517 (1991).
McGuiness, et al, Mol. Microbiol., 7:505-514 (1993).
Rudinger, et al, In: Peptide Hormones. (Ed) JA Parsons. University Park Press (Jun. 1976).
Houghten, et al, Vaccines 86, Cold Spring Harbor Laboratory, p. 21-25 (1986).
Park, et al, In: Proceedings of the 40th Annual Meeting of National Mastitis Council, National Council Incorporated, pp. 247-248 (Feb. 2001).
Hammerschmidt, et al, Infect. Immun. 67:1683-1687 (Apr. 1999).
Staggs, et al, Mol. Microbiol., 12:613-619 (1994).
Biswas, et al, Infect. Immun., 67:455-459 (1999).
Park, HM, et al, "Effect of iron chelators on expression of *Streptococcus uberis* lactoferrin-binding proteins," Database Biosis, Accession No. PREV200200233416 (2001).
Wang, L, et al, "Prokaryotic essential gene 31978," XP-002438045, Database Geneseq, retrieved from EBI Accession No. GSN:ACA50321 (2003).
Smoot, JC, et al, "*Streptococcus pyogenes* strain MGAS8232, section 21 of 173 . . . ," XP-002438021, Database EMBL, retrieved from EBI Accession No. EMBL:AE009973 (2002).

*Primary Examiner*—S. Devi
(74) *Attorney, Agent, or Firm*—Howard Eisenberg, Esq.

(57) ABSTRACT

A polypeptide, designated as "*Streptococcus uberis* Adhesion Molecule" (SUAM), and fragments of SUAM, prevent internalization and adherence of *Streptococcus uberis* and other streptococcal pathogens to cells. The SUAM polypeptide and fragments may be used diagnostically and therapeutically. Nucleic acid sequences encoding the SUAM polypeptide and fragments are included in the invention.

4 Claims, 6 Drawing Sheets

```
ATGATTAGTCTTCTATCCGAATTTGATAGTCATTTGGTAGGAGTGGCTGTTTTTGCTGAAA
ATGCTAAAGAAGAACGTGAACAGATGGCATATAAATCATTGCTTAAAGTTTCTGAAATAG
ATGTCAAGAACAATAAAGTCGTCGTTGAAGTTGGGAATATTTTTAACGATATATAATGTAT
GGAGAGAAAAAGGGAATATTATGGAATTCGAAAACACAAAATCTAATCAGATTAAAACA
ACACTTGCTTTAACGTCAACACTCGCACTTCTTGGAACTGGTGTTGGTATGGGACATACCG
TTAATGCGGATGACATGACAACTGCTGATCAATCACCTAAATTACAAGGTGAAGAAGC
AACATTGGCGCCTACAAACATTGAAGATACTAAAGCAGCCATTGATATTAAAACAGCTAC
ATTAGCAGAACAAACCGATGCTCTTAATACTGTAAATGAGACAATCACAAGCACAAATGA
AGAATTAGCTACTTTAGAAGGAGGCTTAGCTGATAAAGAAACAGCAGTTGCAGATGCTGA
AAAAACATTGGAGTCTGTTTCAAATGCCTCAGAAGAAGAATTTAATCAATTAGCAGAACA
AAATAAAGCTGACTTAGCTAAAACTCAAGAGGAGCTAAAACTTGCTGAAGCAACAAAAG
AAGAAGTTGCAACACAGGTATTGACACAATCTGACGAGGTAACAGCTGCAGCTAATGAAG
CTAAAAAAATGGCTGAAAAAGTTGCACAAGCAGAGACAAAAGTTTCAGACTTGACGAAA
ATGGTCAATCAACCAGAAGCAATAACAGCTCAAGTTGAAATAGAACAAAACAATGTCAA
AATCATTTCGGAAGATTTAGCAAAAGCCAAAACTGATTTAGTTGCTGTAACAGATAATAC
AAAAACACAATTAGCAAATGATTTAGCGACTGCTCAATCTAGCTTAAGTGCCAAACAAA
TGAATTAGCTAAAGTACAGTCACAAACAAGTAATGTCGCAGTGAATGTTATGGGTGCTAA
TAAAATGGTTGCTCCAACTAATTACCCAATTAATGAAATCAAAAAATTAATGTCAAGTGG
TTACATTGGGACACAATCTTATCTAAATACATTCTATGCTTTAAAAGATCAACTGGTTTCT
AAAGCAGAAGTTGGGGCATACTTAAATCATTACGTTGATATCGCAAGTGACTTAAACCGT
ATCGTTAACCCAGATAACTTATCAGTTGAGGTTCAAAATGAATTGGCTGTATTTGCAGCAA
CATTGATTAATTCTGTTCGTCAACAATTTGGTCTTTCTGCAGTCGAAGTGACGCAAGGTGC
TCAAGAGTTTGCTCGCACTTTGACTCGAAACTATAAAGTAACACATGGAAACACTGTTCCT
TTCTTTAATTACAATCAACCTGGCAAGAATGGTCATATAGGCATTGGTCCACACGATAGAA
CAATTATCGAACAAGCAGCTACAAGTGTTGGCTTAAAAGCTAATGATGATAATATGTATG
AAAACATCGGATTCTTTGATGATGTTCATACTGTTAATGGTATCAAACGTAGTATTTATAA
CAGTATTAAGTACATGCTGTTTACAGACTTCACCTATGGAAATACATTTGGACATACGGTT
AACTTGTTGCGTTCTGATAAAACAAACCCAAGTGCTCCGGTCTATTTAGGAGTTTCAACAG
AAACTGTTGGTGGTTTAAATACCCACTATGTTATCTTCCCGGCAAGCAATATTGTAAATGC
CAGCCAATTCAGCAAACAAGTGGTTTCAGGTCCATTAACAACAGTTGATAACAGTGCTAA
AATTAGCACTCTTCAAGCAAGTATTACTTCTGTTGAGTCTAAAATTCAAACCTTACAAAAA
CGTATTGCAAATATTTCTTCAGAAGCACTAGTTGTCTCTGCACAGAGAAAAGTAGATGGTT
TAGCTGCAAAACTTCAAAAAGCTGAATCTAACGTTGAAAAAGCAAAAGCTCAACTTCAAC
AGTTACAAGATTCAAAAGAAGATTTACATAAACAACTTGCTTTTTCCCTTTCAACTCGTAA
GGATTTAAAAGGTCAACTTGACGAATCGCTTGTTCACCTAAATCAGTCTAAAATTCTTTTA
CATAGCTTAGAAGAAAAACAAAGTCAAGTGGCAAGTCAAATTAACGTCTTGACATTGAAG
AAGGCACAACTTGAAAAAGAACTAGCCTTTAACTCTCATCCAAATCGTGAAAAAGTTGCA
AAAGAAAAAGTTGAAGAGGCTCAAAAAGCATTAACAGAAACCTTATCTCAAATTAAAACT
AAAAAAGCTATCTTAAATGATTTAACACAAGAAAAAGCAAAATTGACGTCAGCAATCACA
ACAACTGAACAACAAATTGTTTTGTTGAAGAATCATTTAGCAAATCAAGTGGCGAATGCT
CCAAAAATCAGCAGTATTGTCCAAAGATCAGAAAACAATAGAGTAAGACCTGATGTTTCT
GATACAAGAGAGAAGGCAGTAGATACTGCTCAAGAAGCGACAATTCTTGCTCAAGCAGA
AACAATGGCTGAAGAAGTCATTACAAATTCTGCAAAAGCCATTGTTGCAAATGCTCAAAA
TGTTGCACAAGAGATTATGAAAGTAGCACCTGAAGTAACACCTGATCAAGGAGTTGTTGC
AAAAGTTGCAGATAATATTAAGAAAAATAATGCCCCAGCAAGTAAATCATATGGTGCAAG
TTCATCAACGGTAGGAAATGCTACTTCTTCACGAGATGAAAGTACAAAACGTGCTTTAAG
AGCAGGAATTGTTATGCTGGCAGCAGCAGGACTTACTGGTTACAAACTCAGAAGAGATGG
CAAAAAATAAGAAAATCAAAGGAAAAATTGATTGACAGAAAGTACCGTCTATGTTACTAT
AGTAGACGGTACTTTTTACTTTTGGTCTCTCAAAAGTGTACAGAGACGTGCTGACAATTGT
TGCAAAAGTACACACAGATATAGGCTGTCACCAAGTGCTATATCAACCAAAAATAAAAAA
ATACAGGAGAATGTAGATGCCTACAATTAAC
```

FIGURE 3

LVFYPNLIVIWEWLFLLKMLKKNVNRWHINHCLKFLKMSRTIKSSLKLGIFLTIYNVW
REKGNIMEFENTKSNQIKTTLALTSTLALLGTGVGMGHTVNA<u>DDMTTADQSPKLQ</u>
<u>GEEATLAPT</u>NIEDTKAAIDIKTATLAEQTDALNTVNETITSTNEELATLEGGLADKET
AVADAEKTLESVSNASEEEFNQLAEQNKADLAKTQEELKLAEATKEEVATQVLTQS
DEVTAAANEAKKMAEKVAQAETKVSDLTKMVNQPEAITAQVEIEQNNVKIISEDLA
KAKTDLVAVTDNTKTQLANDLATAQSSLSAKQNELAKVQSQTSNVAVNVMGANK
MVAPTNYPINEIKKLMSSGYIGTQSYLNTFYALKDQLVSKAEVGAYLNHYVDIASDL
NRIVNPDNLSVEVQNELAVFAATLINSVRQQFGLSAVEVTQGAQEFARTLTRNYKVT
HGNTVPFFNYNQPGKNGHIGIGPHDRTIIEQAATSVGLKANDDNMYENIGFFDDVHT
VNGIKRSIYNSIKYMLFTDFTYGNTFGHTVNLLRSDKTNPSAPVYLGVSTETVGGLNT
HYVIFPASNIVNASQFSKQVVSGPLTTVDNSAKISTLQASITSVESKIQTLQKRIANISSE
ALVVSAQRKVDGLAAKLQKAESNVEKAKAQLQQLQDSKEDLHKQLAFSLSTRKDL
KGQLDESLVHLNQSKILLHSLEEKQSQVASQINVLTLKKAQLEKELAFNSHPNREKV
AKEKVEEAQKALTETLSQIKTKKAILNDLTQEKAKLTSAITTTEQQIVLLKNHLANQV
ANAPKISSIVQRSENNRVRPDVSDTREKAVDTAQEATILAQAETMAEEVITNSAKAIV
ANAQNVAQEIMKVAPEVTPDQGVVAKVADNIKKNNAPASKSYGASSSTVGNATSSR
DESTKRALRAGIVMLAAAGLTGYKLRRDGKK-ENQRKN-LTESTVYVTIVDGTFYFW
SLKSVQRRADNCCKSTHRYRLSPSAISTKNKKIQENVDAYN

FIGURE 4

```
GTCATTTGGTAGGAGTGGCTGTTTTTGCTGAAAATGCTAAAGAAGAACGTGAACAGATGG
CATATAAATCATTGCTTAAAGTTTCTGAAATAGATGTCAAGAACAATAAAGTCGTCGTTGA
AGTTGGGAATATTTTTAACGATATATAATGTATGGAGAGAAAAAGGGAATATTATGGAAC
TCGAAAACACAAAATCTAATCAGATTAAAACAACACTTGCTTTAACGTCAACACTCGCAC
TTCTTGGAACTGGTGTTGGTATGGGACATACCGTTAATGCGGATGACATGACAACTGCTG
ATCAATCACCTAAATTACAAGGTGAAGAAGCAACATTGGCGCCTACAAACATTGAAGA
TACTAAAGCAGCCATTGATACTAAAACAGCTACATTAGCAGAACAAACCGATGCTCTTAA
TACTGTAAATGAGACAATCACAAGCACAAATGAAGAATTAGCTACTTTAGAAGGAGGCTT
AGCTGATAAAGAAACAGCAGTTGCAGATGCTGAAAAAACATTGGAGTCTGTTTCAAATGC
CTCAGAAGAAGAATTTAATCAATTAGCAGAACAAAATAAAGCTGACTTAGCTAAAACTCA
AGAGGAGCTAAAACTTGCTGAAGCAACAAAAGAAGAAGTTGCAACACAGGTATTGACAC
AATCTGACGAGGTAACAGCTGCAGCTAATGAAGCTAAAAAAATGGCTGAAAAAGTTGCA
CAAGCAGAGACAAAAGTTTCAGACTTGACGAAAATGGTCAATCAACCAGAAGCAATAAC
AGCTCAAGTTGAAATAGAACAAAACAATGTCAAAATCATTTCGGAAGATTTAGCAAAAGC
CAAAACTGATTTAGTTGCTGTAACAGATAATACAAAAACACAATTAGCAAATGATTTAGC
GACTGCTCAATCTAGCTTAAGTGCCAAACAAAATGAATTAGCTAAAGTACAGTCACAAAC
AAGTAATGTCGCAGTGAATGTTATGGGTGCTAATAAAATGGTTGCTCCAACTAATTACCCA
ATTAATGAAATCAAAAAATTAATGTCAAGTGGTTACATTGGGACACAATCTTATCTAAAT
ACATTCTATGCTTTAAAAGATCAACTGGTTTCTAAAGCAGAAGTTGGGGCATACTTAAATC
ATTACGTTGATATCGCAAGTGACTTAAACCGTATCGTTAACCCAGATAACTTATCAGTTGA
GGTTCAAAATGAATTGGCTGTATTTGCAGCAACATTGATTAATTCTGTTCGTCAGCAATTT
GGTCTTTCTGCAGTCGAAGTGACGCAAGGTGCTCAAGAGTTTGCTCGCACTTTGACTCAAA
ACTATAAAGCAACACATGGAAACACTGTTCCTTTCTTTAATTACAATCAACCTGGCAAGAA
TGGTCATATAGGCATTGGTCCACACGATAGAACAATTATCGAACAAGCAGCTACAAGTGT
TGGCTTAAAAGCTAATGATGATAACATGTATGAAAACATCGGATTCTTTGATGATGTTCAT
ACTGTTAATGGTATCAAACGTAGTATTTATAACAGTATTAAGTACATGCTGTTTACAGACC
TCACCTATGGAAATACATTTGGACATACGGTTAACTTGTTGCGTTCTGATAAAACAAACCC
AAGTGCTCCGGTCTATTTAGGAGTTTCAACAGAAACTGTTGGTGGTTTAAATACCCACTAT
GTTATCTTCCCGGCAAGCAATATTGTAAATGCCAGCCAGTTCAGCAAACAAGTGGTTTCAG
GTCCATTAACAACAGTTGATAACAGTGCTAAAATTAGCACTCTTCAAGCAAGTATTGCTTC
TGTTGAGTCTAAAATTCAAACCTTACAAAAACGTATTGCAAATATTTCTTCAGAAGCACTA
GTTATCTCTGCACAGAGAAAAGTAGATGGTTTAGCTGCAAAACTTCAAAAAGCTGAATCT
AACGTTGAAAAAGCAAAAGCTCAACTTCAACAGTTAAAAGATTCAAAAGAAGATTTACAT
AAACAACTTGCTTTTGCCCTTTCAACTCGTAAGGATTTAAAAGGTCAACTTGACGAATCGC
TTGTTCACCTAAATCAGTCTAAAATTCTTTTTCATAGCTTAGAAGAAAAACAAAGTCAAGT
GGCAAGTCAAATTAACGTCTTGACATTGAAGAAGGCACAACTTGAAAAAGAACTAGCCTT
TAACTCTCATCCAAATCGTGAAAAAGTTGCAAAAGAAAAAGTTGAAGAGGCTCAAAAAG
CATTAACAGAAACCTTATCTCAAATTAAAACTAAAAAAGCTATCTTAAATGATTTAACAC
AAGAAAAAGCAAAATTGACGTCAGCAATCACAACAACTGAACAACAAATTGTTTTGTTGA
AGAATCATTTAGCAAATCAAGTGGCGAATGCTCCAAAAATCAGCAGTATTGTCCAAAGAT
CAGAAAACAATGGAGTAAGACCTGATGTTTCTGATACAAGAGAGAAGGCAGTAGATACT
GCTCAAGAAGCGACAATTCTTGCTCAAGCAGAAACAATGGCTGAAGAAGTCATTACAAAT
TCTGCAAAAGCCATTGTTGCAAATGCTCAAAATGTTGCACAAGAGATTATGAAAGTAGCA
CCTGAAGTAACACCTGATCAAGGAGTTGTTGCAAAAGTTGCAGATAATATTAAGAAAAAT
AATGCCCCAGCAAGTAAATCATATGGTGCAAGTTCATCAACTGTAGGAAATGCTACTTCTT
CACGAGATGAAAGTACAAAACGTGCTTTAAGAGCAGGAATTGTTATGCTGGCAGCAGCAG
GACTTACTGGTTACAAACTCAGAAGAGATGGCAAAAAATAAGAAAATCAAAGGAAAAT
TGATTGACAGAAAGTACCGTCTATGTTACTATAGTAGACGGTACTTTTTACTTTTGGTCTCT
CAAAAGTGTACAGAGACGTGCTGACAATTGTTGCAAAAGTACACACAGATATAGGCTGTC
ACCAAGTGCTATATCAACCA
```

FIGURE 5

ValIleTrp***GluTrpLeuPheLeuLeuLysMetLeuLysLysAsnValAsnArgTrp
HisIleAsnHisCysLeuLysPheLeuLys***MetSerArgThrIleLysSerSerLeu
LysLeuGlyIlePheLeuThrIleTyrAsnValTrpArgGluLysGlyAsnIleMetGlu
LeuGluAsnThrLysSerAsnGlnIleLysThrThrLeuAlaLeuThrSerThrLeuAla
LeuLeuGlyThrGlyValGlyMetGlyHisThrValAsnAla<u>AspAspMetThrThrAla</u>
<u>AspGlnSerProLysLeuGlnGlyGluGluAlaThrLeuAlaProThr</u>AsnIleGluAsp
ThrLysAlaAlaIleAspThrLysThrAlaThrLeuAlaGluGlnThrAspAlaLeuAsn
ThrValAsnGluThrIleThrSerThrAsnGluGluLeuAlaThrLeuGluGlyGlyLeu
AlaAspLysGluThrAlaValAlaAspAlaGluLysThrLeuGluSerValSerAsnAla
SerGluGluGluPheAsnGlnLeuAlaGluGlnAsnLysAlaAspLeuAlaLysThrGln
GluGluLeuLysLeuAlaGluAlaThrLysGluGluValAlaThrGlnValLeuThrGln
SerAspGluValThrAlaAlaAlaAsnGluAlaLysLysMetAlaGluLysValAlaGln
AlaGluThrLysValSerAspLeuThrLysMetValAsnGlnProGluAlaIleThrAla
GlnValGluIleGluGlnAsnAsnValLysIleIleSerGluAspLeuAlaLysAlaLys
ThrAspLeuValAlaValThrAspAsnThrLysThrGlnLeuAlaAsnAspLeuAlaThr
AlaGlnSerSerLeuSerAlaLysGlnAsnGluLeuAlaLysValGlnSerGlnThrSer
AsnValAlaValAsnValMetGlyAlaAsnLysMetValAlaProThrAsnTyrProIle
AsnGluIleLysLysLeuMetSerSerGlyTyrIleGlyThrGlnSerTyrLeuAsnThr
PheTyrAlaLeuLysAspGlnLeuValSerLysAlaGluValGlyAlaTyrLeuAsnHis
TyrValAspIleAlaSerAspLeuAsnArgIleValAsnProAspAsnLeuSerValGlu
ValGlnAsnGluLeuAlaValPheAlaAlaThrLeuIleAsnSerValArgGlnGlnPhe
GlyLeuSerAlaValGluValThrGlnGlyAlaGlnGluPheAlaArgThrLeuThrGln
AsnTyrLysAlaThrHisGlyAsnThrValProPhePheAsnTyrAsnGlnProGlyLys
AsnGlyHisIleGlyIleGlyProHisAspArgThrIleIleGluGlnAlaAlaThrSer
ValGlyLeuLysAlaAsnAspAspAsnMetTyrGluAsnIleGlyPhePheAspAspVal
HisThrValAsnGlyIleLysArgSerIleTyrAsnSerIleLysTyrMetLeuPheThr
AspLeuThrTyrGlyAsnThrPheGlyHisThrValAsnLeuLeuArgSerAspLysThr
AsnProSerAlaProValTyrLeuGlyValSerThrGluThrValGlyGlyLeuAsnThr
HisTyrValIlePheProAlaSerAsnIleValAsnAlaSerGlnPheSerLysGlnVal
ValSerGlyProLeuThrThrValAspAsnSerAlaLysIleSerThrLeuGlnAlaSer
IleAlaSerValGluSerLysIleGlnThrLeuGlnLysArgIleAlaAsnIleSerSer
GluAlaLeuValIleSerAlaGlnArgLysValAspGlyLeuAlaAlaLysLeuGlnLys
AlaGluSerAsnValGluLysAlaLysAlaGlnLeuGlnGlnLeuLysAspSerLysGlu
AspLeuHisLysGlnLeuAlaPheAlaLeuSerThrArgLysAspLeuLysGlyGlnLeu
AspGluSerLeuValHisLeuAsnGlnSerLysIleLeuPheHisSerLeuGluGluLys
GlnSerGlnValAlaSerGlnIleAsnValLeuThrLeuLysLysAlaGlnLeuGluLys
GluLeuAlaPheAsnSerHisProAsnArgGluLysValAlaLysGluLysValGluGlu
AlaGlnLysAlaLeuThrGluThrLeuSerGlnIleLysThrLysLysAlaIleLeuAsn
AspLeuThrGlnGluLysAlaLysLeuThrSerAlaIleThrThrThrGluGlnGlnIle
ValLeuLeuLysAsnHisLeuAlaAsnGlnValAlaAsnAlaProLysIleSerSerIle
ValGlnArgSerGluAsnAsnGlyValArgProAspValSerAspThrArgGluLysAla
ValAspThrAlaGlnGluAlaThrIleLeuAlaGlnAlaGluThrMetAlaGluGluVal
IleThrAsnSerAlaLysAlaIleValAlaAsnAlaGlnAsnValAlaGlnGluIleMet
LysValAlaProGluValThrProAspGlnGlyValValAlaLysValAlaAspAsnIle
LysLysAsnAsnAlaProAlaSerLysSerTyrGlyAlaSerSerSerThrValGlyAsn
AlaThrSerSerArgAspGluSerThrLysArgAlaLeuArgAlaGlyIleValMetLeu
AlaAlaAlaGlyLeuThrGlyTyrLysLeuArgArgAspGlyLysLys***GluAsnGln
ArgLysAsn***LeuThrGluSerThrValTyrValThrIleValAspGlyThrPheTyr
PheTrpSerLeuLysSerValGlnArgArgAlaAspAsnCysCysLysSerThrHisArg
TyrArgLeuSerProSerAlaIleSerThr

FIGURE 6

SEQUENCE LISTING

<160> NUMBER OF SEQ ID NOS: 17

<210> SEQ ID NO 1
<211> LENGTH: 3041
<212> TYPE: DNA
<213> ORGANISM: Streptococcus uberis

<400> SEQUENCE: 1

```
atgattagtc ttctatccga atttgatagt catttggtag gagtggctgt ttttgctgaa      60
aatgctaaag aagaacgtga acagatggca tataaatcat tgcttaaagt ttctgaaata     120
gatgtcaaga caataaagt cgtcgttgaa gttgggaata tttttaacga tatataatgt     180
atggagagaa aagggaata ttatggaatt cgaaaacaca aaatctaatc agattaaaac     240
aacacttgct ttaacgtcaa cactcgcact tcttggaact ggtgttggta tgggacatac     300
cgttaatgcg gatgacatga caactgctga tcaatcacct aaattacaag gtgaagaagc     360
aacattggcg cctacaaaca ttgaagatac taaagcagcc attgatatta aaacagctac     420
attagcagaa caaccgatg ctcttaatac tgtaaatgag acaatcacaa gcacaaatga     480
agaattagct actttagaag gaggcttagc tgataaagaa acagcagttg cagatgctga     540
aaaaacattg gagtctgttt caaatgcctc agaagaagaa tttaatcaat tagcagaaca     600
aaataaagct gacttagcta aaactcaaga ggagctaaaa cttgctgaag caacaaaaga     660
agaagttgca acacaggtat tgacacaatc tgacgaggta acagctgcag ctaatgaagc     720
taaaaaaatg gctgaaaaag ttgcacaagc agagacaaaa gtttcagact tgacgaaaat     780
ggtcaatcaa ccagaagcaa taacagctca agttgaaata gaacaaaaca atgtcaaaat     840
catttcggaa gatttagcaa aagccaaaac tgatttagtt gctgtaacag ataatacaaa     900
aacacaatta gcaaatgatt tagcgactgc tcaatctagc ttaagtgcca aacaaaatga     960
attagctaaa gtacagtcac aaacaagtaa tgtcgcagtg aatgttatgg gtgctaataa    1020
aatggttgct ccaactaatt acccaattaa tgaaatcaaa aaattaatgt caagtggtta    1080
cattgggaca caatcttatc taaatacatt ctatgcttta aaagatcaac tggtttctaa    1140
agcagaagtt ggggcatact taaatcatta cgttgatatc gcaagtgact taaaccgtat    1200
cgttaaccca gataacttat cagttgaggt tcaaaatgaa ttggctgtat ttgcagcaac    1260
attgattaat tctgttcgtc aacaatttgg tctttctgca gtcgaagtga cgcaaggtgc    1320
tcaagagttt gctcgcactt tgactcgaaa ctataaagta acacatggaa acactgttcc    1380
tttctttaat tacaatcaac ctggcaagaa tggtcatata ggcattggtc cacgcgatag    1440
aacaattatc gaacaagcag ctacaagtgt tggcttaaaa gctaatgatg ataatatgta    1500
tgaaaacatc ggattctttg atgatgttca tactgttaat ggtatcaaac gtagtattta    1560
taacagtatt aagtacatgc tgtttacaga cttcacctat ggaaatacat ttggacatac    1620
ggttaacttg ttgcgttctg ataaaacaaa cccaagtgct ccggtctatt taggagtttc    1680
aacagaaact gttggtggtt taaatacca ctatgttatc ttcccggcaa gcaatattgt    1740
aaatgccagc caattcagca acaagtggt ttcaggtcca ttaacaacag ttgataacag    1800
tgctaaaatt agcactcttc aagcaagtat tacttctgtt gagtctaaaa ttcaaacctt    1860
acaaaaacgt attgcaaata tttcttcaga agcactagtt gtctctgcac agagaaaagt    1920
agatggtttta gctgcaaaac ttcaaaaagc tgaatctaac gttgaaaaag caaaagctca    1980
acttcaacag ttacaagatt caaaagaaga tttacataaa caacttgctt tttcccttc    2040
```

-continued

```
aactcgtaag gatttaaaag gtcaacttga cgaatcgctt gttcacctaa atcagtctaa      2100
aattctttta catagcttag aagaaaaaca aagtcaagtg gcaagtcaaa ttaacgtctt      2160
gacattgaag aaggcacaac ttgaaaaaga actagccttt aactctcatc caaatcgtga      2220
aaaagttgca aaagaaaaag ttgaagaggc tcaaaaagca ttaacagaaa ccttatctca      2280
aattaaaact aaaaaagcta tcttaaatga tttaacacaa gaaaaagcaa aattgacgtc      2340
agcaatcaca acaactgaac aacaaattgt tttgttgaag aatcatttag caaatcaagt      2400
ggcgaatgct ccaaaaatca gcagtattgt ccaaagatca gaaaacaata gagtaagacc      2460
tgatgtttct gatacaagag agaaggcagt agatactgct caagaagcga caattcttgc      2520
tcaagcagaa acaatggctg aagaagtcat tacaaattct gcaaaagcca ttgttgcaaa      2580
tgctcaaaat gttgcacaag agattatgaa agtagcacct gaagtaacac ctgatcaagg      2640
agttgttgca aaagttgcag ataatattaa gaaaaataat gccccagcaa gtaaatcata      2700
tggtgcaagt tcatcaacgg taggaaatgc tacttcttca cgagatgaaa gtacaaaacg      2760
tgctttaaga gcaggaattg ttatgctggc agcagcagga cttactggtt acaaactcag      2820
aagagatggc aaaaaataag aaaatcaaag gaaaaattga ttgacagaaa gtaccgtcta      2880
tgttactata gtagacggta cttttttactt ttggtctctc aaaagtgtac agagacgtgc      2940
tgacaattgt tgcaaaagta cacacagata taggctgtca ccaagtgcta tatcaaccaa      3000
aaataaaaaa atacaggaga atgtagatgc ctacaattaa c                          3041
```

<210> SEQ ID NO 2
<211> LENGTH: 1007
<212> TYPE: PRT
<213> ORGANISM: Streptococcus uberis

<400> SEQUENCE: 2

```
Leu Val Phe Tyr Pro Asn Leu Ile Val Ile Trp Glu Trp Leu Phe Leu
  1               5                  10                  15

Leu Lys Met Leu Lys Lys Asn Val Asn Arg Trp His Ile Asn His Cys
             20                  25                  30

Leu Lys Phe Leu Lys Met Ser Arg Thr Ile Lys Ser Ser Leu Lys Leu
         35                  40                  45

Gly Ile Phe Leu Thr Ile Tyr Asn Val Trp Arg Glu Lys Gly Asn Ile
     50                  55                  60

Met Glu Phe Glu Asn Thr Lys Ser Asn Gln Ile Lys Thr Thr Leu Ala
 65                  70                  75                  80

Leu Thr Ser Thr Leu Ala Leu Leu Gly Thr Gly Val Gly Met Gly His
                 85                  90                  95

Thr Val Asn Ala Asp Asp Met Thr Thr Ala Asp Gln Ser Pro Lys Leu
            100                 105                 110

Gln Gly Glu Glu Ala Thr Leu Ala Pro Thr Asn Ile Glu Asp Thr Lys
        115                 120                 125

Ala Ala Ile Asp Ile Lys Thr Ala Thr Leu Ala Glu Gln Thr Asp Ala
    130                 135                 140

Leu Asn Thr Val Asn Glu Thr Ile Thr Ser Thr Asn Glu Glu Leu Ala
145                 150                 155                 160

Thr Leu Glu Gly Gly Leu Ala Asp Lys Glu Thr Ala Val Ala Asp Ala
                165                 170                 175

Glu Lys Thr Leu Glu Ser Val Ser Asn Ala Ser Glu Glu Glu Phe Asn
            180                 185                 190
```

-continued

```
Gln Leu Ala Glu Gln Asn Lys Ala Asp Leu Ala Lys Thr Gln Glu Glu
        195                 200                 205

Leu Lys Leu Ala Glu Ala Thr Lys Glu Glu Val Ala Thr Gln Val Leu
    210                 215                 220

Thr Gln Ser Asp Glu Val Thr Ala Ala Asn Glu Ala Lys Lys Met
225                 230                 235                 240

Ala Glu Lys Val Ala Gln Ala Glu Thr Lys Val Ser Asp Leu Thr Lys
                245                 250                 255

Met Val Asn Gln Pro Glu Ala Ile Thr Ala Gln Val Glu Ile Glu Gln
            260                 265                 270

Asn Asn Val Lys Ile Ile Ser Glu Asp Leu Ala Lys Ala Lys Thr Asp
        275                 280                 285

Leu Val Ala Val Thr Asp Asn Thr Lys Thr Gln Leu Ala Asn Asp Leu
    290                 295                 300

Ala Thr Ala Gln Ser Ser Leu Ser Ala Lys Gln Asn Glu Leu Ala Lys
305                 310                 315                 320

Val Gln Ser Gln Thr Ser Asn Val Ala Val Asn Val Met Gly Ala Asn
                325                 330                 335

Lys Met Val Ala Pro Thr Asn Tyr Pro Ile Asn Glu Ile Lys Lys Leu
            340                 345                 350

Met Ser Ser Gly Tyr Ile Gly Thr Gln Ser Tyr Leu Asn Thr Phe Tyr
        355                 360                 365

Ala Leu Lys Asp Gln Leu Val Ser Lys Ala Glu Val Gly Ala Tyr Leu
    370                 375                 380

Asn His Tyr Val Asp Ile Ala Ser Asp Leu Asn Arg Ile Val Asn Pro
385                 390                 395                 400

Asp Asn Leu Ser Val Glu Val Gln Asn Glu Leu Ala Val Phe Ala Ala
                405                 410                 415

Thr Leu Ile Asn Ser Val Arg Gln Gln Phe Gly Leu Ser Ala Val Glu
            420                 425                 430

Val Thr Gln Gly Ala Gln Glu Phe Ala Arg Thr Leu Thr Arg Asn Tyr
        435                 440                 445

Lys Val Thr His Gly Asn Thr Val Pro Phe Phe Asn Tyr Asn Gln Pro
    450                 455                 460

Gly Lys Asn Gly His Ile Gly Ile Gly Pro His Asp Arg Thr Ile Ile
465                 470                 475                 480

Glu Gln Ala Ala Thr Ser Val Gly Leu Lys Ala Asn Asp Asp Asn Met
                485                 490                 495

Tyr Glu Asn Ile Gly Phe Phe Asp Asp Val His Thr Val Asn Gly Ile
            500                 505                 510

Lys Arg Ser Ile Tyr Asn Ser Ile Lys Tyr Met Leu Phe Thr Asp Phe
        515                 520                 525

Thr Tyr Gly Asn Thr Phe Gly His Thr Val Asn Leu Leu Arg Ser Asp
    530                 535                 540

Lys Thr Asn Pro Ser Ala Pro Val Tyr Leu Gly Val Ser Thr Glu Thr
545                 550                 555                 560

Val Gly Gly Leu Asn Thr His Tyr Val Ile Phe Pro Ala Ser Asn Ile
                565                 570                 575

Val Asn Ala Ser Gln Phe Ser Lys Gln Val Val Ser Gly Pro Leu Thr
            580                 585                 590

Thr Val Asp Asn Ser Ala Lys Ile Ser Thr Leu Gln Ala Ser Ile Thr
        595                 600                 605

Ser Val Glu Ser Lys Ile Gln Thr Leu Gln Lys Arg Ile Ala Asn Ile
```

```
                      610                 615                 620
Ser Ser Glu Ala Leu Val Val Ser Ala Gln Arg Lys Val Asp Gly Leu
625                 630                 635                 640

Ala Ala Lys Leu Gln Lys Ala Glu Ser Asn Val Glu Lys Ala Lys Ala
                645                 650                 655

Gln Leu Gln Gln Leu Gln Asp Ser Lys Glu Asp Leu His Lys Gln Leu
                660                 665                 670

Ala Phe Ser Leu Ser Thr Arg Lys Asp Leu Lys Gly Gln Leu Asp Glu
                675                 680                 685

Ser Leu Val His Leu Asn Gln Ser Lys Ile Leu Leu His Ser Leu Glu
690                 695                 700

Glu Lys Gln Ser Gln Val Ala Ser Gln Ile Asn Val Leu Thr Leu Lys
705                 710                 715                 720

Lys Ala Gln Leu Glu Lys Glu Leu Ala Phe Asn Ser His Pro Asn Arg
                725                 730                 735

Glu Lys Val Ala Lys Glu Lys Val Glu Ala Gln Lys Ala Leu Thr
                740                 745                 750

Glu Thr Leu Ser Gln Ile Lys Thr Lys Lys Ala Ile Leu Asn Asp Leu
                755                 760                 765

Thr Gln Glu Lys Ala Lys Leu Thr Ser Ala Ile Thr Thr Glu Gln
                770                 775                 780

Gln Ile Val Leu Leu Lys Asn His Leu Ala Asn Gln Val Ala Asn Ala
785                 790                 795                 800

Pro Lys Ile Ser Ser Ile Val Gln Arg Ser Glu Asn Asn Arg Val Arg
                805                 810                 815

Pro Asp Val Ser Asp Thr Arg Glu Lys Ala Val Asp Thr Ala Gln Glu
                820                 825                 830

Ala Thr Ile Leu Ala Gln Ala Glu Thr Met Ala Glu Glu Val Ile Thr
                835                 840                 845

Asn Ser Ala Lys Ala Ile Val Ala Asn Ala Gln Asn Val Ala Gln Glu
                850                 855                 860

Ile Met Lys Val Ala Pro Glu Val Thr Pro Asp Gln Gly Val Val Ala
865                 870                 875                 880

Lys Val Ala Asp Asn Ile Lys Lys Asn Ala Pro Ala Ser Lys Ser
                885                 890                 895

Tyr Gly Ala Ser Ser Thr Val Gly Asn Ala Thr Ser Ser Arg Asp
                900                 905                 910

Glu Ser Thr Lys Arg Ala Leu Arg Ala Gly Ile Val Met Leu Ala Ala
                915                 920                 925

Ala Gly Leu Thr Gly Tyr Lys Leu Arg Arg Asp Gly Lys Lys Glu Asn
                930                 935                 940

Gln Arg Lys Asn Leu Thr Glu Ser Thr Val Tyr Val Thr Ile Val Asp
945                 950                 955                 960

Gly Thr Phe Tyr Phe Trp Ser Leu Lys Ser Val Gln Arg Arg Ala Asp
                965                 970                 975

Asn Cys Cys Lys Ser Thr His Arg Tyr Arg Leu Ser Pro Ser Ala Ile
                980                 985                 990

Ser Thr Lys Asn Lys Lys Ile Gln Glu Asn Val Asp Ala Tyr Asn
                995                 1000                1005
```

<210> SEQ ID NO 3
<211> LENGTH: 2971
<212> TYPE: DNA
<213> ORGANISM: Streptococcus uberis

<400> SEQUENCE: 3

```
gtcatttggt aggagtggct gttttgctg aaaatgctaa agaagaacgt gaacagatgg        60
catataaatc attgcttaaa gtttctgaaa tagatgtcaa gaacaataaa gtcgtcgttg       120
aagttgggaa tattttaac gatatataat gtatggagag aaaaagggaa tattatggaa        180
ctcgaaaaca caaatctaa tcagattaaa acaacacttg ctttaacgtc aacactcgca        240
cttcttggaa ctggtgttgg tatgggacat accgttaatg cggatgacat gacaactgct       300
gatcaatcac ctaaattaca aggtgaagaa gcaacattgg cgcctacaaa cattgaagat       360
actaaagcag ccattgatac taaaacagct acattagcag aacaaaccga tgctcttaat       420
actgtaaatg agacaatcac aagcacaaat gaagaattag ctactttaga aggaggctta       480
gctgataaag aaacagcagt tgcagatgct gaaaaaacat tggagtctgt ttcaaatgcc       540
tcagaagaag aatttaatca attagcagaa caaaataaag ctgacttagc taaaactcaa       600
gaggagctaa aacttgctga agcaacaaaa gaagaagttg caacacaggt attgacacaa       660
tctgacgagg taacagctgc agctaatgaa gctaaaaaaa tggctgaaaa agttgcacaa       720
gcagagacaa aagtttcaga cttgacgaaa atggtcaatc aaccagaagc aataacagct       780
caagttgaaa tagaacaaaa caatgtcaaa atcatttcgg aagatttagc aaaagccaaa       840
actgatttag ttgctgtaac agataataca aaaacacaat tagcaaatga tttagcgact       900
gctcaatcta gcttaagtgc caaacaaaat gaattagcta agtacgtc acaaacaagt        960
aatgtcgcag tgaatgttat gggtgctaat aaaatggttg ctccaactaa ttacccaatt      1020
aatgaaatca aaaattaat gtcaagtggt tacattggga cacaatctta tctaaataca       1080
ttctatgctt taaaagatca actggtttct aaagcagaag ttggggcata cttaaatcat      1140
tacgttgata tcgcaagtga cttaaaccgt atcgttaacc cagataactt atcagttgag      1200
gttcaaaatg aattggctgt atttgcagca acattgatta attctgttcg tcagcaattt      1260
ggtctttctg cagtcgaagt gacgcaaggt gctcaagagt ttgctcgcac tttgactcaa      1320
aactataaag caacacatgg aaacactgtt cctttcttta attacaatca acctggcaag      1380
aatggtcata taggcattgg tccacacgat agaacaatta tcgaacaagc agctacaagt      1440
gttggcttaa aagctaatga tgataacatg tatgaaaaca tcggattctt tgatgatgtt      1500
catactgtta atggtatcaa acgtagtatt tataacagta ttaagtacat gctgtttaca      1560
gacctcacct atggaaatac atttggacat acggttaact tgttgcgttc tgataaaaca      1620
aacccaagtg ctccggtcta tttaggagtt tcaacagaaa ctgttggtgg tttaaatacc      1680
cactatgtta tcttcccggc aagcaatatt gtaaatgcca gccagttcag caaacaagtg      1740
gtttcaggtc cattaacaac agttgataac agtgctaaaa ttagcactct tcaagcaagt      1800
attgcttctg ttgagtctaa aattcaaacc ttacaaaaac gtattgcaaa tatttcttca      1860
gaagcactag ttatctctgc acagagaaaa gtagatggtt tagctgcaaa acttcaaaaa      1920
gctgaatcta acgttgaaaa agcaaaagct caacttcaac agttaaaaga ttcaaaagaa      1980
gatttacata acaacttgc ttttgcccct tcaactcgta aggatttaaa aggtcaactt       2040
gacgaatcgc ttgttcacct aaatcagtct aaaattcttt ttcatagctt agaagaaaaa      2100
caaagtcaag tggcaagtca aattaacgtc ttgcattga agaggcaca acttgaaaaa        2160
gaactagcct ttaactctca tccaaatcgt gaaaagttg caaagaaaa agttgaagag        2220
gctcaaaaag cattaacaga aaccttatct caaattaaaa ctaaaaaagc tatcttaaat     2280
```

-continued

```
gatttaacac aagaaaaagc aaaattgacg tcagcaatca caacaactga acaacaaatt    2340
gttttgttga agaatcattt agcaaatcaa gtggcgaatg ctccaaaaat cagcagtatt    2400
gtccaaagat cagaaaacaa tggagtaaga cctgatgttt ctgatacaag agagaaggca    2460
gtagatactg ctcaagaagc gacaattctt gctcaagcag aaacaatggc tgaagaagtc    2520
attacaaatt ctgcaaaagc cattgttgca aatgctcaaa atgttgcaca agagattatg    2580
aaagtagcac ctgaagtaac acctgatcaa ggagttgttg caaaagttgc agataatatt    2640
aagaaaaata atgccccagc aagtaaatca tatggtgcaa gttcatcaac tgtaggaaat    2700
gctacttctt cacgagatga agtacaaaa cgtgctttaa gagcaggaat tgttatgctg    2760
gcagcagcag gacttactgg ttacaaactc agaagagatg caaaaaata gaaaatcaa    2820 aggaaaaatt gattgacaga agtaccgtc tatgttacta tagtagacgg tacttttac    2880 ttttggtctc tcaaaagtgt acagagacgt gctgacaatt gttgcaaaag tacacacaga    2940
tataggctgt caccaagtgc tatatcaacc a                                  2971
```

<210> SEQ ID NO 4
<211> LENGTH: 15
<212> TYPE: PRT
<213> ORGANISM: Streptococcus uberis

<400> SEQUENCE: 4

Met Thr Thr Ala Asp Gln Ser Pro Lys Leu Gln Gly Glu Glu Ala
1               5                   10                  15

<210> SEQ ID NO 5
<211> LENGTH: 45
<212> TYPE: DNA
<213> ORGANISM: Streptococcus uberis

<400> SEQUENCE: 5
atgacaactg ctgatcaatc acctaaatta caaggtgaag aagca                   45

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
gtcatttggt aggagtggct g                                             21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
tggttgatat agcacttggt gac                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8

-continued

```
ggatgacatg acaactgctg atc                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 9
caattgtcag cacgtctctg tac                                              23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 10
cttggaactg gtgttggtat gg                                               22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
caggtgttac ttcaggtgct ac                                               22

<210> SEQ ID NO 12
<211> LENGTH: 20
<212> TYPE: PRT
<213> ORGANISM: Streptococcus uberis
<220> FEATURE:
<221> NAME/KEY: MOD_RES
<222> LOCATION: (17)
<223> OTHER INFORMATION: Thr or Ala
<220> FEATURE:
<221> NAME/KEY: MOD_RES
<222> LOCATION: (19)
<223> OTHER INFORMATION: Ile or Ala
<220> FEATURE:
<221> NAME/KEY: MOD_RES
<222> LOCATION: (20)
<223> OTHER INFORMATION: Val or Lys

<400> SEQUENCE: 12

Asp Met Thr Thr Ala Asp Gln Ser Pro Lys Leu Gln Gly Glu Glu Ala
 1               5                  10                  15

Xaa Leu Xaa Xaa
            20

<210> SEQ ID NO 13
<211> LENGTH: 3
<212> TYPE: PRT
<213> ORGANISM: Streptococcus uberis

<400> SEQUENCE: 13

Val Ile Trp
 1

<210> SEQ ID NO 14
<211> LENGTH: 26
<212> TYPE: PRT
```

```
<213> ORGANISM: Streptococcus uberis

<400> SEQUENCE: 14

Glu Trp Leu Phe Leu Leu Lys Met Leu Lys Lys Asn Val Asn Arg Trp
1               5                   10                  15

His Ile Asn His Cys Leu Lys Phe Leu Lys
            20                  25

<210> SEQ ID NO 15
<211> LENGTH: 905
<212> TYPE: PRT
<213> ORGANISM: Streptococcus uberis

<400> SEQUENCE: 15

Met Ser Arg Thr Ile Lys Ser Ser Leu Lys Leu Gly Ile Phe Leu Thr
1               5                   10                  15

Ile Tyr Asn Val Trp Arg Glu Lys Gly Asn Ile Met Glu Leu Glu Asn
            20                  25                  30

Thr Lys Ser Asn Gln Ile Lys Thr Thr Leu Ala Leu Thr Ser Thr Leu
        35                  40                  45

Ala Leu Leu Gly Thr Gly Val Gly Met Gly His Thr Val Asn Ala Asp
    50                  55                  60

Asp Met Thr Thr Ala Asp Gln Ser Pro Lys Leu Gln Gly Glu Glu Ala
65                  70                  75                  80

Thr Leu Ala Pro Thr Asn Ile Glu Asp Thr Lys Ala Ala Ile Asp Thr
                85                  90                  95

Lys Thr Ala Thr Leu Ala Glu Gln Thr Asp Ala Leu Asn Thr Val Asn
            100                 105                 110

Glu Thr Ile Thr Ser Thr Asn Glu Glu Leu Ala Thr Leu Glu Gly Gly
        115                 120                 125

Leu Ala Asp Lys Glu Thr Ala Val Ala Asp Ala Glu Lys Thr Leu Glu
    130                 135                 140

Ser Val Ser Asn Ala Ser Glu Glu Phe Asn Gln Leu Ala Glu Gln
145                 150                 155                 160

Asn Lys Ala Asp Leu Ala Lys Thr Gln Glu Glu Leu Lys Leu Ala Glu
                165                 170                 175

Ala Thr Lys Glu Glu Val Ala Thr Gln Val Leu Thr Gln Ser Asp Glu
            180                 185                 190

Val Thr Ala Ala Ala Asn Glu Ala Lys Lys Met Ala Glu Lys Val Ala
        195                 200                 205

Gln Ala Glu Thr Lys Val Ser Asp Leu Thr Lys Met Val Asn Gln Pro
    210                 215                 220

Glu Ala Ile Thr Ala Gln Val Glu Ile Glu Gln Asn Asn Val Lys Ile
225                 230                 235                 240

Ile Ser Glu Asp Leu Ala Lys Ala Lys Thr Asp Leu Val Ala Val Thr
                245                 250                 255

Asp Asn Thr Lys Thr Gln Leu Ala Asn Asp Leu Ala Thr Ala Gln Ser
            260                 265                 270

Ser Leu Ser Ala Lys Gln Asn Glu Leu Ala Lys Val Gln Ser Gln Thr
        275                 280                 285

Ser Asn Val Ala Val Asn Val Met Gly Ala Asn Lys Met Val Ala Pro
    290                 295                 300

Thr Asn Tyr Pro Ile Asn Glu Ile Lys Lys Leu Met Ser Ser Gly Tyr
305                 310                 315                 320

Ile Gly Thr Gln Ser Tyr Leu Asn Thr Phe Tyr Ala Leu Lys Asp Gln
```

-continued

```
                325                 330                 335
Leu Val Ser Lys Ala Glu Val Gly Ala Tyr Leu Asn His Tyr Val Asp
                340                 345                 350
Ile Ala Ser Asp Leu Asn Arg Ile Val Asn Pro Asp Asn Leu Ser Val
                355                 360                 365
Glu Val Gln Asn Glu Leu Ala Val Phe Ala Ala Thr Leu Ile Asn Ser
                370                 375                 380
Val Arg Gln Gln Phe Gly Leu Ser Ala Val Glu Val Thr Gln Gly Ala
385                 390                 395                 400
Gln Glu Phe Ala Arg Thr Leu Thr Gln Asn Tyr Lys Ala Thr His Gly
                405                 410                 415
Asn Thr Val Pro Phe Phe Asn Tyr Asn Gln Pro Gly Lys Asn Gly His
                420                 425                 430
Ile Gly Ile Gly Pro His Asp Arg Thr Ile Ile Glu Gln Ala Ala Thr
                435                 440                 445
Ser Val Gly Leu Lys Ala Asn Asp Asp Asn Met Tyr Glu Asn Ile Gly
                450                 455                 460
Phe Phe Asp Asp Val His Thr Val Asn Gly Ile Lys Arg Ser Ile Tyr
465                 470                 475                 480
Asn Ser Ile Lys Tyr Met Leu Phe Thr Asp Leu Thr Tyr Gly Asn Thr
                485                 490                 495
Phe Gly His Thr Val Asn Leu Leu Arg Ser Asp Lys Thr Asn Pro Ser
                500                 505                 510
Ala Pro Val Tyr Leu Gly Val Ser Thr Glu Thr Val Gly Gly Leu Asn
                515                 520                 525
Thr His Tyr Val Ile Phe Pro Ala Ser Asn Ile Val Asn Ala Ser Gln
                530                 535                 540
Phe Ser Lys Gln Val Val Ser Gly Pro Leu Thr Thr Val Asp Asn Ser
545                 550                 555                 560
Ala Lys Ile Ser Thr Leu Gln Ala Ser Ile Ala Ser Val Glu Ser Lys
                565                 570                 575
Ile Gln Thr Leu Gln Lys Arg Ile Ala Asn Ile Ser Ser Glu Ala Leu
                580                 585                 590
Val Ile Ser Ala Gln Arg Lys Val Asp Gly Leu Ala Ala Lys Leu Gln
                595                 600                 605
Lys Ala Glu Ser Asn Val Glu Lys Ala Lys Ala Gln Leu Gln Gln Leu
                610                 615                 620
Lys Asp Ser Lys Glu Asp Leu His Lys Gln Leu Ala Phe Ala Leu Ser
625                 630                 635                 640
Thr Arg Lys Asp Leu Lys Gly Gln Leu Asp Glu Ser Leu Val His Leu
                645                 650                 655
Asn Gln Ser Lys Ile Leu Phe His Ser Leu Glu Glu Lys Gln Ser Gln
                660                 665                 670
Val Ala Ser Gln Ile Asn Val Leu Thr Leu Lys Lys Ala Gln Leu Glu
                675                 680                 685
Lys Glu Leu Ala Phe Asn Ser His Pro Asn Arg Glu Lys Val Ala Lys
                690                 695                 700
Glu Lys Val Glu Glu Ala Gln Lys Ala Leu Thr Glu Thr Leu Ser Gln
705                 710                 715                 720
Ile Lys Thr Lys Lys Ala Ile Leu Asn Asp Leu Thr Gln Glu Lys Ala
                725                 730                 735
Lys Leu Thr Ser Ala Ile Thr Thr Glu Gln Gln Ile Val Leu Leu
                740                 745                 750
```

```
Lys Asn His Leu Ala Asn Gln Val Ala Asn Ala Pro Lys Ile Ser Ser
        755                 760                 765
Ile Val Gln Arg Ser Glu Asn Asn Gly Val Arg Pro Asp Val Ser Asp
        770                 775                 780
Thr Arg Glu Lys Ala Val Asp Thr Ala Gln Glu Ala Thr Ile Leu Ala
785                 790                 795                 800
Gln Ala Glu Thr Met Ala Glu Glu Val Ile Thr Asn Ser Ala Lys Ala
                805                 810                 815
Ile Val Ala Asn Ala Gln Asn Val Ala Gln Glu Ile Met Lys Val Ala
                820                 825                 830
Pro Glu Val Thr Pro Asp Gln Gly Val Val Ala Lys Val Ala Asp Asn
        835                 840                 845
Ile Lys Lys Asn Asn Ala Pro Ala Ser Lys Ser Tyr Gly Ala Ser Ser
        850                 855                 860
Ser Thr Val Gly Asn Ala Thr Ser Ser Arg Asp Glu Ser Thr Lys Arg
865                 870                 875                 880
Ala Leu Arg Ala Gly Ile Val Met Leu Ala Ala Ala Gly Leu Thr Gly
                885                 890                 895
Tyr Lys Leu Arg Arg Asp Gly Lys Lys
                900                 905

<210> SEQ ID NO 16
<211> LENGTH: 6
<212> TYPE: PRT
<213> ORGANISM: Streptococcus uberis

<400> SEQUENCE: 16

Glu Asn Gln Arg Lys Asn
1               5

<210> SEQ ID NO 17
<211> LENGTH: 46
<212> TYPE: PRT
<213> ORGANISM: Streptococcus uberis

<400> SEQUENCE: 17

Leu Thr Glu Ser Thr Val Tyr Val Thr Ile Val Asp Gly Thr Phe Tyr
1               5                   10                  15
Phe Trp Ser Leu Lys Ser Val Gln Arg Arg Ala Asp Asn Cys Cys Lys
                20                  25                  30
Ser Thr His Arg Tyr Arg Leu Ser Pro Ser Ala Ile Ser Thr
                35                  40                  45
```

STREPTOCOCCUS UBERIS ADHESION MOLECULE

The invention was developed in part by a research grant from the United States Department of Agriculture and the U.S. government may therefore have certain rights to the invention.

This application claims the priority of U.S. patent application Ser. No. 10/691,384, filed on Oct. 22, 2003, which issued as U.S. Pat. No. 7,517,955 on Apr. 14, 2009, which claims priority from U.S. Provisional Patent Application Ser. No. 60/429,499, filed on Nov. 26, 2002.

FIELD OF THE INVENTION

The invention pertains generally to the field of antigenic proteins and polypeptides.

Specifically, the invention pertains to the field of polypeptides that are useful to diagnose the presence of an infection and to elicit an immune response against a bacterial pathogen, especially streptococcal pathogens.

BACKGROUND OF THE INVENTION

*Streptococcus* is a genus of bacteria that causes disease in humans and other animals.

In humans, one of the most important streptococcal pathogens is *Streptococcus pyogenes*, the causative organism of strep throat, scarlet fever, and rheumatic fever. In cattle, streptococcal infections are a significant cause of disease, such as mastitis.

Mastitis affects virtually every dairy farm and has been estimated to affect 38% of all cows. The disease causes destruction of milk-synthesizing tissues which reduces milk production and alters milk composition. In severe cases, the productive performance of dairy cattle may be diminished permanently. Thus, mastitis continues to be the single greatest impediment to profitable dairy production. Losses associated with mastitis cost American dairy producers about 2 billion dollars per year and cost dairy producers worldwide an estimated 25 billion dollars per year.

Current mastitis control programs devised in the 1960's are based primarily on hygiene including teat disinfection, antibiotic therapy and culling of chronically infected cows. Acceptance and application of these measures has led to considerable progress in controlling contagious mastitis pathogens such as *Streptococcus agalactiae* and *Staphylococcus aureus*. However, postmilking teat disinfection and antibiotic dry cow therapy have been less effective against environmental mastitis pathogens. Studies have shown that as the prevalence of contagious mastitis pathogens was reduced, the proportion of intramammary infections (IMI) by environmental pathogens increased markedly.

Therefore, it is not surprising that environmental mastitis has become a major problem in many well-managed dairy farms that have successfully controlled contagious pathogens. In these herds, environmental streptococci account for a significant number of both subclinical and clinical IMI in lactating and nonlactating cows. Environmental *Streptococcus* species involved in bovine mastitis include *Streptococcus uberis*, *Streptococcus dysgalactiae* subsp. *dysgalactiae*, *Streptococcus equinus* (formerly referred to as *Streptococcus bovis*), *Streptococcus equi*, *Streptococcus parauberis* and *Streptococcus canis*. Among the environmental streptococci, *S. uberis* and *S. dysgalactiae* subsp. *dysgalactiae* appear to be the most prevalent, infecting mammary glands as favorable conditions arise.

In spite of the economic impact caused by the high prevalence of environmental streptococci in many well-managed dairy herds, virulence factors associated with pathogenesis of environmental streptococcal mastitis in dairy cows are not well understood. This constitutes a major obstacle for development of strategies to control these important mastitis pathogens. Consequently, strategies for controlling mastitis caused by environmental streptococci are poorly defined and currently inadequate.

A significant need exists for effective therapies to combat streptococcal infections, both in domestic animals and in people, and for effective modalities by which the presence of a streptococcal infection may be definitively diagnosed.

Survival of pathogenic microorganisms, such as Streptococci, has depended on the evolution of a range of strategies for evasion of host defenses. Associated with this evolution is the expression of a variety of virulence determinants that favor persistence of bacteria in the face of a massive inflammatory cell infiltration. In the case of bovine mastitis, it is hypothesized that adherence to and subsequent internalization of mastitis pathogens into mammary epithelial cells is an important early event in the establishment of new intramammary infections in lactating and nonlactating mammary glands of dairy cows. Virulence factors that favor adherence and internalization to host cells play a crucial role in the establishment, spread, and persistence of infection. During the last decade, research from our laboratory has focused extensively on development of in vivo and in vitro models to study host-pathogen interactions, and especially on identification and characterization of virulence factors associated with the pathogenesis of *S. uberis* mastitis.

BRIEF DESCRIPTION OF THE FIGURES

FIG. 3 is the theoretically elucidated SUAM gene sequence. (Seq. ID No. 1)

FIG. 4 shows the translation of the nucleotide sequence of Seq. ID No. 1 in the correct reading frame. (Seq. ID No. 2)

FIG. 5 is the DNA sequence of the SUAM gene. (Seq. ID No. 3)

FIG. 6 shows the translation of the nucleotide sequence of Seq. ID No. 3 in the correct reading frame. (Seq. ID No. 13 to Seq. No. 17)

DESCRIPTION OF THE INVENTION

Figure 1:
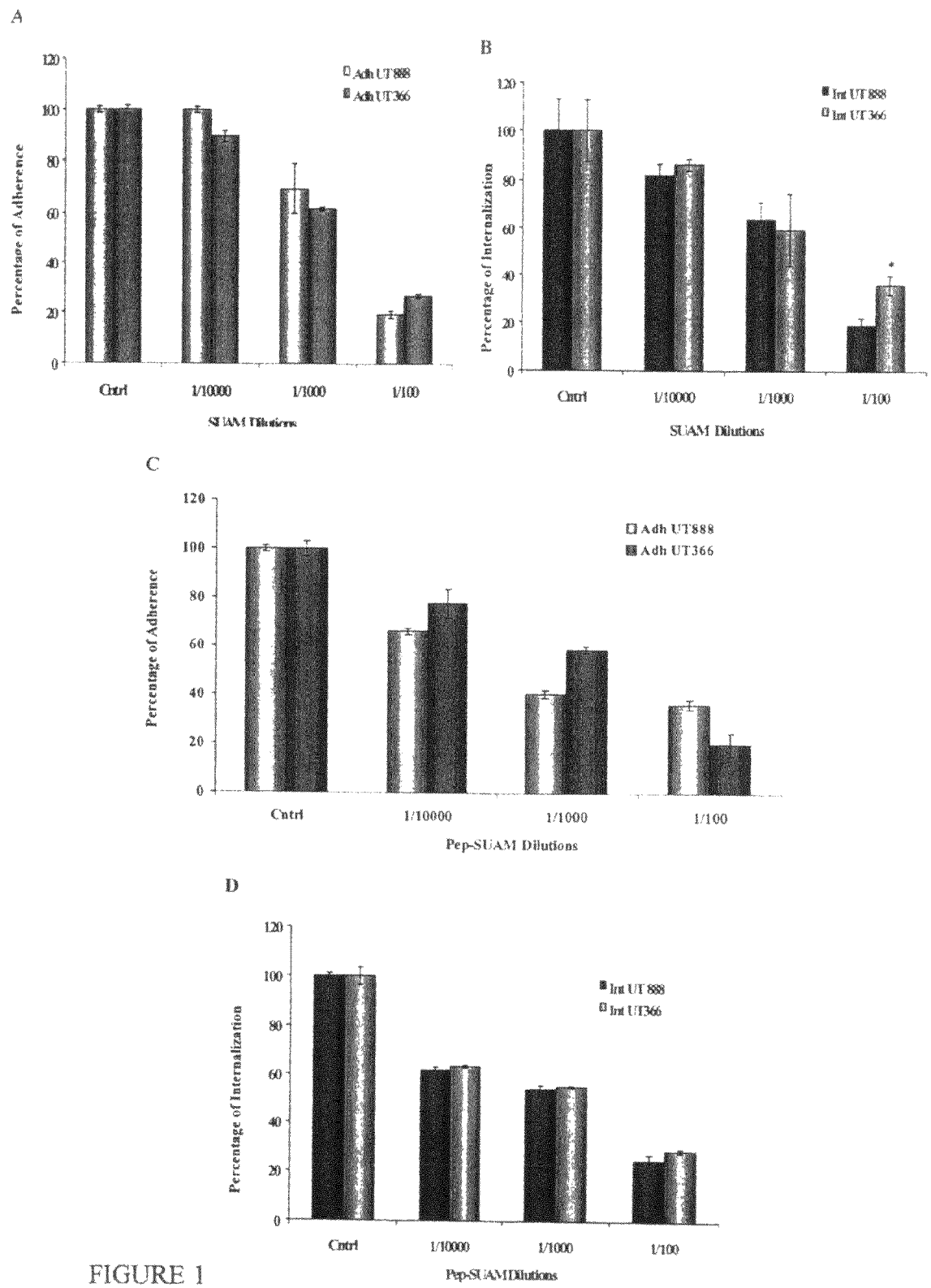
FIG. 1A-1D is a series of bar graphs showing the effects of antibodies directed against SUAM (A and B) and pepSUAM (C and D) on adherence and internalization of *S. uberis* into bovine mammary epithelial cells.

In this application, the terms "*Streptococcus uberis* Adhesion Molecule" or "SUAM" is preferably used although the terms "*Streptococcus* Lactoferrin-binding Protein", "Lactoferrin Binding Protein" and "LBP" are also used to refer to the same polypeptide. The terms "*Streptococcus uberis* Adhesion Molecule" and "SUAM" are preferred so as not to confuse the polypeptide of the present invention with the protein identified as "*Streptococcus uberis* Lactoferrin-Binding Protein" in Jiang et al., WO 98/21231. The Jiang protein is a different protein than the SUAM of the present invention. Protein-nucleic acid TBLASTN (National Center for Biotechnology Information) and Swissprot amino acid data bank were used to align the SUAM N-terminal amino acid sequence with previously sequenced genes and proteins including *S. uberis* LBP described by Jiang et al. No similarities were found, thus indicating that the SUAM bacterial protein of the invention is novel.

Recently, it has been shown that *S. uberis* binds to purified bovine milk lactoferrin (LF) and that at least two proteins from *S. uberis* were involved in this binding. Fang and Oliver, FEMS Microbiol. Lett., 176:91 (1999). It has further been shown that LF appears to function as a bridging molecule between *S. uberis* and bovine mammary epithelial cells, facilitating adherence of this mastitis pathogen to host cells. Fang, et al., American Journal of Veterinary Research, 61:275 (2000). This research indicates that the *S. uberis* proteins that bind to LF influence adherence of *S. uberis* to mammary epithelial cells and internalization of *S. uberis* into bovine mammary epithelial cells.

Further research in our laboratory has provided the following discoveries.

(1) A 112 kDA protein from *S. uberis* that binds to LF was isolated and purified and an N-terminal amino acid sequence of this 112 kDa protein was determined. The sequence is that of a novel protein, which is referred to herein as *Streptococcus uberis* Adhesion Molecule or SUAM.

(2) SUAM-like proteins were identified in other Streptococci, including *Streptococcus* dysgalactiae subsp. *dysgalactiae* and *Streptococcus agalactiae*.

(3) The SUAM-like proteins produced by *S. dysgalactiae* subsp. *dysgalactiae* bind to bovine LF in a manner similar to that which occurs with *S. uberis*.

(4) Antibodies against SUAM (whole protein) and to a synthetic peptide (pepSUAM) encompassing 15 amino acids near the N-terminus of SUAM have been produced.

(5) These antibodies cross-react with homologous proteins present in other strains of *S. uberis* demonstrating that SUAM was produced by all strains of *S. uberis* evaluated.

(6) Anti-pepSUAM and anti-SUAM antibodies cross-react with other streptococcal pathogens, including *S. agalactiae*, *S. dysgalactiae* subsp. *dysgalactiae*, and *Streptococcus pyogenes*.

(7) Antibodies directed against pepSUAM or SUAM inhibit adherence of *S. uberis* to, and internalization of *S. uberis* into, bovine mammary epithelial cells. This establishes that pepSUAM and SUAM are biologically active and are involved in adherence to and internalization of *S. uberis* into bovine mammary epithelial cells, indicating the importance of SUAM as a significant *S. uberis* virulence factor.

(8) A theoretical DNA sequence of SUAM was determined and confirmed by PCR and restriction digests.

(9) The "true" DNA sequence encoding for SUAM was elucidated and found to have 99% homology to the theoretically elucidated SUAM DNA.

It is conceived that this single virulence factor (SUAM) plays a critical role in the pathogenesis of streptococcal mastitis by facilitating bacterial adherence to bovine mammary epithelial cells. It is conceived that *S. uberis* expresses SUAM and uses LF in milk and/or on the epithelial cell surface to adhere to mammary epithelial cells. It is further conceived that antibodies that bind to SUAM or pepSUAM may be used to diagnose infections due to *S. uberis* or other streptococci or to treat infections due to *S. uberis* or other streptococci. It is further conceived that nucleic acid sequences that encode SUAM or pepSUAM may be used diagnostically or in the production of anti-streptococcal vaccines. It is further conceived that the SUAM and pepSUAM polypeptides of the invention may be used to in the production of antisera or vaccines to combat diseases due to *S. uberis* or other streptococci.

In one embodiment, the invention is a polypeptide comprising an amino acid sequence of at least 6 sequential amino acids of pepSUAM (MTTADQSPKLQGEEA), designated herein as Seq. ID No. 4, wherein an antibody that binds to the polypeptide inhibits adherence to and/or internalization of *S. uberis* into bovine mammary epithelial cells. For example the 6 sequential amino acids of the polypeptide of the invention may be amino acids 1 to 6, 2 to 7, 3 to 8, 4 to 9, 5 to 10, 6 to 11, 7 to 12, 8 to 13, 9 to 14, or 10 to 15 of Seq. ID No. 4 pepSUAM.

Preferably, the polypeptide of this embodiment of the invention comprises an amino acid sequence of more than 6 sequential amino acids of pepSUAM of Seq. ID No. 4, for example, 7, 8, 9, 10, 11, 12, 13, 14 sequential amino acids, or the entire 15 amino acid sequence of Seq. ID No. 4. The polypeptide of the invention may further contain additional amino acids to the amino terminal or carboxy terminal sides of the sequence that is a portion or all of pepSUAM. For example, the polypeptide of the invention may contain at its amino terminal end the amino acids DD, which are present at the amino terminal end of full-length SUAM.

The polypeptide may be used to elicit antibodies which may be used to diagnose infections due to SUAM-expressing organisms such as *Streptococcus*, like *S. uberis*. The polypeptide may also be used to elicit an immune response in an animal or human that is susceptible to infection by an organism that contains a surface antigen that will bind to an antibody that binds to the polypeptide of the invention. Thus, the polypeptide of the invention may be useful as a vaccine against infection due to *Streptococcus*, such as *S. uberis*, *S. pyogenes*, *S. agalactiae*, or *S. dysgalactiae*.

In another embodiment, the invention is an isolated SUAM protein preferably having the amino acid sequence shown in FIG. 4 or FIG. 6 and designated herein as Seq. ID No. 2 or Seq. ID No. 15, respectively.

In another embodiment, the invention is a polypeptide derived from SUAM protein, which may be isolated by the method described below and which comprises the sequence of amino acids MTTADQSPKLQGEEA, Seq. ID No. 4.

The invention also includes polypeptides that are substantially homologous with the pepSUAM polypeptide or SUAM protein and polypeptides derived therefrom, as described above. As used in this context, the term "substantially homologous" means that the amino acid sequence shares at least 50%, such as at least 60%, preferably at least 70%, more preferably at least 80%, and most preferably at least 90% amino acid identity with the pepSUAM or SUAM protein or polypeptides derived therefrom and wherein an antibody that binds to the polypeptide inhibits the adherence and/or the internalization of *S. uberis* to bovine mammary epithelial cells.

In another embodiment, the invention is an antibody that selectively binds to an amino acid sequence of any 6 to 15 sequential amino acids of pepSUAM, as described above. Preferably, the antibody inhibits the adherence and/or the internalization of *S. uberis* to bovine mammary epithelial cells. The antibody may be a monoclonal or polyclonal antibody and may be used diagnostically or therapeutically.

In another embodiment, the invention is an antibody that selectively binds to the SUAM polypeptides or proteins of the invention. Preferably, the antibody inhibits the adherence and/or the internalization of *S. uberis* to bovine mammary epithelial cells. The antibody may be a monoclonal or polyclonal antibody and may be used diagnostically or therapeutically.

In another embodiment, the invention is an isolated nucleic acid sequence that encodes the pepSUAM polypeptide. Preferably, the nucleic acid sequence comprises the sequence shown in underline and in bold in FIG. 3, and designated Seq. ID No. 5: ATGACAACTGCTGATCAATCACCTAAAT-TACAAGGTGAAGAAGCA.

In another embodiment, the invention is an isolated nucleic acid sequence that encodes the SUAM protein. Preferably, the nucleic acid sequence comprises either of the sequence shown in FIG. 3 or 5, designated Seq. ID No. 1 and Seq. ID No. 3, respectively. More preferably, the nucleic acid sequence comprises the sequence from nucleotide 317 to nucleotide 2836 of Seq. ID No. 1 or from nucleotide 289 to nucleotide 2808 of Seq. ID No. 3. Most preferably, the nucleic acid sequence comprises the sequence from nucleotide 311 to nucleotide 2836 of Seq. ID No. 1 or nucleotide 283 to nucleotide 2808 of Seq. ID No. 3.

Also included in the isolated nucleic acid sequences of the invention is a nucleic acid sequence that will hybridize under highly stringent conditions, for example at 3×SSC at 65° C. and preferably at 6×SSC at 65° C., to the complement of the above specifically described nucleic acid sequences.

In another embodiment, the invention is a method for immunizing an animal or human with an antigen against a bacterial organism. In accordance with the method of the invention, the polypeptide of the invention or the SUAM polypeptide is administered to an animal or human subject by any suitable means such as by injection or intramammary infusion and the subject is thereby caused to produce antibodies that selectively bind thereto, which antibodies inhibit bacteria that bind to lactoferrin from adhering and/or internalizing to cells and/or enhance clearance of bacterial pathogens. In this way, the ability of the microorganism to cause disease is reduced.

In another embodiment, the invention is a primer selected from the group of

```
(a)   5'-GTC ATT TGG TAG GAG TGG CTG-3',     (Seq. ID No 6)

(b)   5'-TGG TTG ATA TAG CAC TTG GTG AC-3',  (Seq. ID No 7)

(c)   5'-GGA TGA CAT GAC AAC TGC TGA TC-3',  (Seq. ID No 8)

(d)   5'-CAA TTG TCA GCA CGT CTC TGT AC-3',  (Seq. ID No 9)

(e)   5'-CTT GGA ACT GGT GTT GGT ATG G-3',   (Seq. ID No 10)
and (f)   5'-CAG GTG TTA CTT CAG GTG CTA C-3'.   (Seq. ID No 11)
```

Preferably, the primers are grouped in pairs with primers (a) and (b) being paired as a forward and reverse PCR primer, respectively, primers (c) and (d) being paired as a forward and reverse PCR primer, respectively, and primers (e) and (f) being paired as a forward and reverse PCR primer, respectively.

The primers and primer pairs of the invention are useful, for example, in identifying microorganisms that produce SUAM or a polypeptide molecule having a high degree of homology to SUAM, such as 70% or more homology. As such, the primers of the invention may be used to diagnose the presence of an infection with a SUAM polypeptide, or SUAM-like polypeptide, producing microorganism. It is conceived that an animal or human patient that is diagnosed in this manner may be treated with administration of the polypeptide of the invention to induce an immune response against such microorganism.

Following is a list of possible applications of various embodiments of the invention.

This list is not intended to be all inclusive as those skilled in the art will understand that additional uses exist for the invention.

I. Antibodies to SUAM and pepSUAM

A. Commercial Use

Diagnostic

Microbiology: immuno-fluorescence, card-test for preliminary confirmation (including cow-side rapid tests using milk from cows with mastitis)

Serology: Agglutination/precipitation tests (cow-side rapid tests), ELISA Diagnostic enrichment of bacteria from crude samples Treatment/Prevention Therapy for cows with mastitis (systemic/intramammary)

Prevention for new cows introduced to a farm with history of S. uberis infection Intramammary preparations for cows near parturition B. Research Use 1. Isolation/purification of SUAM
2. In vitro pathogenicity assays
3. Recombinant protein expression (monitoring and isolation)
4. Mutant detection
5. Immuno-histochemistry
6. Western blot
7. Immunoprecipitation for protein/protein interaction studies
8. Steric inhibition studies II. SUAM Protein A. Commercial Use 1. Vaccine production
2. Antisera production
3. Protein as antigen component of multivalent vaccine B. Research Use 1. Antisera production
2. Experimental vaccination studies
3. Protein as antigen component of multivalent vaccine
4. Protein as ligand in affinity purification of bovine lactoferrin III. pepSUAM A. Commercial Use 1. Vaccine production
2. Antisera production
3. Peptide as antigen component of multivalent vaccine
4. Peptide as competitive inhibitor of adhesion/invasion in intramammary preps B. Research Use 1. Antisera production
2. Experimental vaccination studies
3. Peptide as component of multivalent vaccine
4. Peptide as ligand in affinity purification of Bovine Lactoferrin IV. SUAM DNA Sequence A. Commercial Use Diagnostic 1. Probes
2. PCR (alternative primers design)
3. Cow-side rapid test (i.e., cantilever)

Prevention of Mastitis
1. Recombinant expression for vaccine production (baculovirus cloning and expression)
2. DNA vaccines (cloning into retro-virus vectors or *Agrobacterium tumefaciens*)
3. Cloning and expression in vitro for vaccine production B. Research Use
1. Probes
2. PCR (alternative primers design)
3. Real time PCR for selection and identification of strains
4. DNA microarrays/differential display (to identify and study factors that enhance or repress SUAM expression)
5. Site directed mutagenesis
6. Production of avirulent carrier strain for this or any other expressed protein vaccine.

V. SUAM PCR Primers

A. Commercial Use

Diagnostic
1. PCR amplification products detected by any means
2. Real time PCR (taq-man, beacons, etc.)
3. Probes B. Research Use
1. PCR Detection
2. Real time PCR (taq-man, beacons, etc.)
3. Probes for southerns, reverse transcriptase protection assays, etc.
4. Cloning and expression The invention is further illustrated in the following non-limiting examples.

EXAMPLE 1

Identification of *Streptococcus Uberis* Lactoferrin-binding Proteins (Prior Art), (Described in Fang, W., and S. P. Oliver, FEMS Microbiol. Lett. 176:91) (1999)

Experiments were conducted to examine binding of lactoferrin (LF) by strains of *S. uberis* causing bovine mastitis and to identify proteins from the bacteria involved in LF-binding. Four strains of *S. uteris* isolated originally from dairy cows with mastitis and *S. uberis* ATCC13387 (American Type Culture Collection, Manassas, Va.) were evaluated. After growth, bacterial cultures were washed and split into two equal portions: one for incubation in milk and the other in phosphate buffered saline (PBS) (as controls). Bacterial surface proteins from pellets were extracted using 0.2% sodium dodecyl sulfate (SDS) and electrophoresed. Gels were silver-stained or transferred onto nitrocellulose membranes for immunoblotting using rabbit anti-bovine LF antibody and HRP (horseradish peroxidase)-conjugated donkey anti-rabbit IgG antibody as probes.

Biotin-avidin-based binding assay (BABA) and ELISA-based binding assay were carried out on immobilized *S. uberis* microplates. LF from bovine milk and transferrin (TF) from bovine plasma were biotinylated. For the BABA assay, serial 2-fold dilutions of biotinylated LF were added into microplate wells. incubated, washed, and probed with HRP-NEUTRAVIDIN. The ELISA-based assay was essentially the same as BABA except that serial 2-fold dilutions of unlabelled LF were substituted for biotinylated LF. Rabbit anti-bovine LF antibody and HRP-conjugated donkey anti-rabbit IgG antibody were used as probes. Inhibition of LF-binding by unlabelled LF, TF, mannose, galactose, and lactose were also tested using BABA and ELISA.

Polypeptides that bound to LF were identified by SDS-PAGE and western blot analysis of bacterial surface proteins. Blots were probed sequentially with LF, rabbit anti-bovine LF antibody, and HRP-conjugated donkey anti-rabbit IgG antibody. At least two proteins in each strain of *S. uberis* were identified as lactoferrin-binding proteins. These included 52 and ~112 kDa bands in 4 of 5 strains evaluated. One strain of *S. uberis* did not have the 112 kDa protein band, however, this strain produced a higher molecular weight protein (134 kDa) which also bound to LF.

The microplate-based assay systems demonstrated that *S. uberis* bound to purified LF. These studies provided evidence that *S. uberis* binds to LF in milk and that at least two proteins from *S. uberis* surface molecules are involved in LF-binding.

Example 2

Effect of Lactoferrin on Adherence of *Streptococcus Uberis* to Bovine Mammary epithelial cells (prior art) (described in Fang, W., R. A. Almeida, and S. P. Oliver, Am. J. Vet. Res. 61:275) (2000)

A series of experiments were conducted to determine effects of LF on adherence of *S. uberis* to mammary epithelial cells. Three strains of *S. uberis* were used. In the first experiment, we investigated the effect of LF on adherence of *S. uberis* to bovine mammary epithelial cells. Sterile LF in Dulbecco's Modified Eagle Medium (DMEM) or milk (0.5 ml) and 0.5 ml of bacterial suspension containing $1-2 \times 10^8$ cfu/ml in DMEM were added to bovine mammary epithelial cell line (MAC-T) monolayers. Final concentrations for LF were 0, 0.01, 0.1 and 1 mg/ml. Those for milk were 0, 12.5%, 25% and 50%. Bacteria were allowed to adhere to MAC-T cells and supernatants were then aspirated and diluted for bacterial counting. Monolayers were washed and lysed, and cell lysates were 10-fold diluted for bacterial counting. *Streptococcus uberis* cultures were also pretreated with LF (1 mg/ml) or milk (100%) for 1 h. Bacterial suspensions in PBS (without LF or milk) were included as controls. Bacteria were then washed and adjusted to $1-2 \times 10^8$ cfu/ml for adherence assays.

To test the effect of anti-bovine LF antibody on adherence, a *S. uberis* strain was pretreated with LF or milk as described above and examined for its adherence to MAC-T cells in presence of different dilutions of rabbit anti-bovine LF antibody. For the microscopic adherence assay, strains of *S. uberis* were labeled with fluorescein isothiocyanate (FITC). FITC-labeled bacteria were resuspended in DMEM. Sterile LF in DMEM (0.15 ml) and FITC labeled bacteria (0.15 ml) were added to wells of chamber slides containing confluent MAC-T cell monolayers. After incubation, bacterial supernatants were removed, and slides were washed and examined microscopically.

All strains of *S. uberis* evaluated bound to LF in milk and to purified LF. LF and milk enhanced adherence of *S. uberis* to MAC-T cells when present in the test medium ($P<0.05-0.01$) except for one strain of *S. uberis*. Pretreatment of bacteria with LF and milk increased adherence of one strain of *S. uberis* ($P<0.01$), but not the other two strains. It is conceived that differences between LF or milk pretreatment and presence of LF or milk in the medium could partially account for the different results. Because LF is synthesized and secreted by mammary epithelial cells and also binds to mammary epithelial cells, it is conceived that the presence of LF in the test medium might enhance the potential of LF as a bridging molecule between bacteria and MAC-T cells, thus increasing adherence. Additionally, differences of intrinsic surface properties among *S. uberis* strains might affect their interaction with LF as well as with MAC-T cells. There were differences among these *S. uberis* strains in hydrophobicity. Two strains of *S. uberis* were more attracted to hexadecane as well as to MAC-T cells than was a third strain of *S. uberis*.

The involvement of milk in the adherence of *S. uberis* to MAC-T cells may be more complicated than that of purified LF because of the coexistence of other milk components that may also play a part in bacterial interactions with epithelial cells. For example, our laboratory demonstrated and reported that adherence to extracellular matrix proteins, particularly collagen, enhanced adherence and internalization of *S. uberis* to bovine mammary epithelial cells and that presence of these host proteins up-regulated expression of ligands for collagen. Therefore, LF is not the only host protein that binds to *S. uberis*. However, our data indicate specific involvement of LF in adherence since addition of rabbit anti-bovine LF antibody significantly decreased adherence of LF or milk-pretreated bacteria to MAC-T cells (P<0.01) at dilutions below 1:500 for LF and 1:100 for milk.

The results of these studies indicate that LF functions as a bridging molecule between *S. uberis* and bovine mammary epithelial cells and facilitates adherence of this mastitis pathogen to the host cells.

EXAMPLE 3

Investigation of Influence of Strain of *S. uberis* on the Enhancing Effect of LF on Adherence and Internalization to Mammary Epithelial Cells To further investigate a possible strain influence on the enhancing effect of LF on adherence and internalization to mammary epithelial cells, additional studies were conducted. In these studies, six strains of *S. uberis* isolated originally from milk of dairy cows with mastitis were used. Bacteria were pretreated with LF (ICN, Aurora, Ohio), 21.4% iron saturation and 97.5% protein content, 1 mg/ml) for 1 h at 37° C., washed 3 times with PBS (pH 7.4), resuspended in DMEM and cocultured with MAC-T cells for 1 h. After incubation, supernatants were removed, monolayers were washed and either lysed with trypsin/triton solution to determine total cell associated bacteria or treated with antibiotic solution to determine internalization of bacteria into mammary epithelial cells. For the latter, after 2 h of incubation, antibiotic solution was removed, monolayers were washed 3 times with PBS and cells were lysed with trypsin/triton solution. Colony forming units per ml (CFU/ml) in lysates were determined using standard colony counting techniques. Although differences in adherence and internalization were detected among strains, addition of LF caused significantly greater adherence or internalization to mammary epithelial cells of all strains of *S. uberis* evaluated.

It is conceived that adherence and internalization are not two separate independent events. Adherent bacteria are quickly internalized through an endocytic-like mechanism, where receptors for the "bridging" proteins are recycled and exposed in or on the host cell surface. The kinetics of these events has been described as a chain reaction where adherence promotes internalization. Therefore, higher concentrations of the "bridging" protein results in increased adherence that in turn leads to increased internalization rather that reversal of adherence. Thus, increased binding of LF by *S. uberis* mediated by a lactoferrin binding protein (SUAM) results in increased bacterial internalization into mammary epithelial cells.

Figure 2:
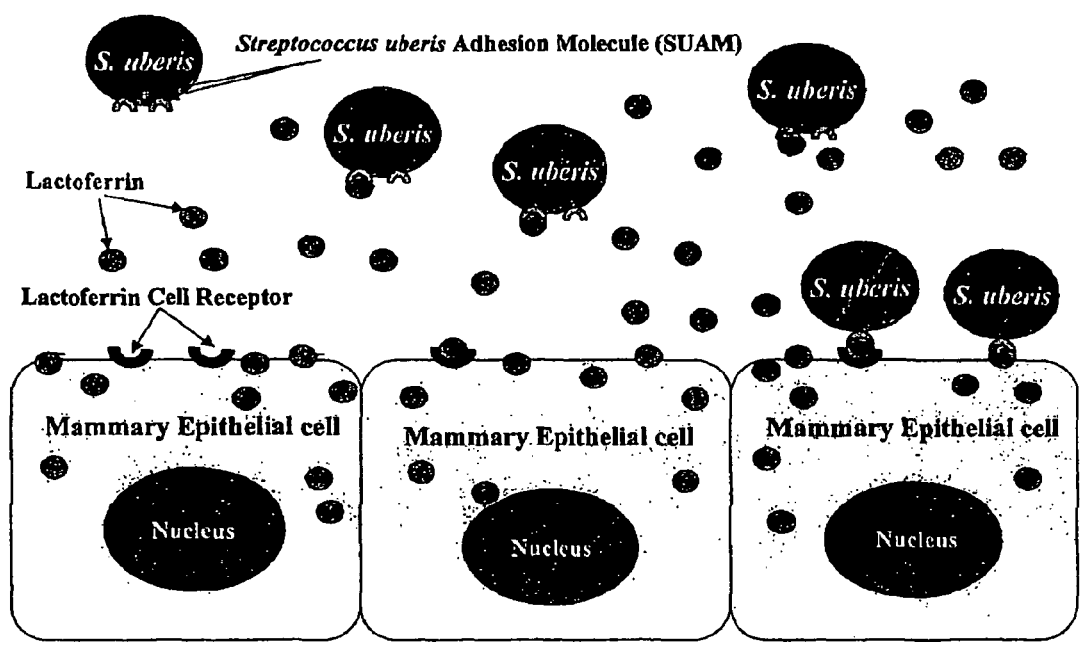
FIG. 2 is a diagrammatic representation of a proposed lactoferrin bridge model for adherence of *Streptococcus uberis* to bovine mammary epithelial cells.

Thus, it is conceived that, by a mechanism referred to herein as "molecular bridging" LF possesses different binding domains, a binding domain for the host cell and another binding domain for *S. uberis* (see the schematic presented in FIG. 2 "Diagram 1"). The interaction between host cell receptor and the host-domain region in *S. uberis* bound LF allows contact of the bacterium and host cell surface membrane resulting in adherence. The interaction between LF and its host cell receptor triggers arrangements on the host membrane that initiate the internalization of the bacterium into the host cell.

EXAMPLE 4

Isolation, Purification and N-terminal Amino-acid Sequencing of *Streptococcus uberis* Adhesion Molecule (SUAM)

A study was conducted to compare potential differences in the efficiency of extraction of SUAM with mutanolysin or SDS by SDS-PAGE and Western blotting. Four strains of *S. uberis* were used. Bacterial surface proteins from cell pellets were extracted from 0.2% SDS in PBS (pH 7.2) following the method described by Fang and Oliver (1999). Each strain of *S. uberis* was grown in THB (Todd-Hewitt Broth) (Difco Laboratories, Detroit, Mich.) at 37° C. overnight. After centrifugation, bacteria were resuspended in PBS. Bacterial pellets were washed three times with sterile PBS, and surface proteins were extracted using 0.2% SDS (sodium dodecyl sulfate) (Bio-Rad Laboratories, Hercules, Calif.; 30 mg wet weight of bacteria per 100 μl of 0.2% SDS) for 1 h at 37° C.

In the mutanolysin extraction method, a modified procedure was used. Bacterial cells were suspended (1 g/2 ml) in 50 mM phosphate buffer (pH 7.2), containing 0.5 M sucrose and 10 mg/ml lysozyme (Sigma, St. Louis, Mo.). The resulting suspension was divided into 2 ml aliquots and 250 units of mutanolysin (N-acetylmuramidase, Sigma) were added per aliquot.

The suspension was shaker incubated for 1 h at 37° C. Bacteria were pelleted by centrifugation and supernatants of each were removed and stored at −20° C.

Extracted bacterial surface proteins (10 μg/lane) were electrophoresed on 10% SDS-PAGE. Gels were stained with Coomassie brilliant blue or transferred onto nitrocellulose membrane using Trans-Blot SD Semi-Dry Electrophoretic Transfer Cell (Bio-Rad, Hercules, Calif.). Unbound sites on blots were blocked with 3% casitone. Blots were probed with LF (ICN, 5 μg/ml) in PBS TWEEN 20 (PBST) containing 0.1% casitone for 6 h at 4° C. followed by four washes with PBST. Procedures for further probing of blots with rabbit anti-bovine LF antibody and HRP-conjugated donkey anti-rabbit IgG antibody were as described previously (Fang and Oliver, 1999). Blots without probing with LF and rabbit anti-bovine LF antibody were included as negative controls.

When surface proteins were extracted with 0.2% SDS detergent and evaluated by SDS-PAGE, 110 kDa and 112 kDa protein bands were extracted more efficiently compared to the mutanolysin extraction method. In Western blot analysis, the intensity of SUAM bands in SDS extracts, particularly 110 and 112 kDa, were much stronger than those of mutanolysin extracts. Results of this study indicate that SDS extracts proteins of interest (110 kDa and 112 kDa) more efficiently and is a preferred method for SUAM purification and subsequent characterization.

EXAMPLE 5

Iron Availability Influences Expression of SUAM

A study was conducted in which the effect of an iron chelator on expression of *S. uberis* was evaluated. Strains of *S. uberis* were grown either in THB or THB treated with the iron chelator 2,2-dipyridyl and surface proteins from bacterial pellets were analyzed by Western blot using LF as a probe and rabbit anti-bovine LF antibody. Western blot analysis showed two major bands of 110 KDa and 112 KDa, respectively, with LF-binding activity.

In addition, LF-binding activity decreased in the presence of an iron chelator which indicates that iron in the medium influences expression of SUAM.

EXAMPLE 6

Purification of SUAM

Thirty ml of PBS (pH 7.4) containing 30 mg of SDS-extracted *S. uberis* surface proteins were loaded into a bovine LF-coupled CNBr-activated SEPHAROSE 4B column. SDS-extracted surface proteins were incubated with shaking for 2 h at 4° C. with 7 ml of SEPHAROSE 4B covalently linked to bovine LF (ICN, 21.4% iron saturation and 97.5% protein content). The LF-SEPHAROSE 4B slurry was loaded into a chromatography column (1.25 cm ×9 cm; total volume 70 ml) (Pfizer, New York, N.Y.). The column was subsequently washed with 10 volumes of TBS (50 mM TRIS-HCl (pH 7.4) +150 mM NaCl containing 0.1% TRITON X 100) to remove nonspecific-binding proteins using a peristaltic pump at a flow rate of 1 ml/min until absorbance at 280 nm approached zero. The column was eluted with a sodium chloride gradient from 0.1 M to 1 M NaCl in TBS. Fractions (10ml/fraction) were analyzed by absorbance at 280 nm, SDS-PAGE and Western blot using LF, rabbit anti-bovine LF antibodies and biotinylated LF as probes. Fractions containing SUAM were pooled, dialyzed against PBS and stored at −70° C. until use.

Analysis of fractions revealed the presence of a protein in fraction number 14 to 32 eluted at 0.5 M NaCl. The molecular mass was estimated to be ~112 kDa using GEL SCAN (Corbett Research, Mortlake, NSW, Australia). Results from SDS-PAGE and Western blot analysis indicated that this band had LF-binding affinity. The yield of purified SUAM was 20 Fg/ml (total 10 ml) from 3 liters of THB-grown *S. uberis* .

Example 7

N-Terminal Amino Acid Sequence of the 112 kDa SUAM

Excised PVDF membrane (PerkinElmer Life and Analytical Sciences, Inc., Boston, Mass.) containing ~ 112 kDa SUAM band was analyzed. The protein was sequenced on an Applied Biosystems model 477A sequencer (Applied Biosystems, Foster City, Calif.) equipped with on-line PTH analysis using the regular program O3RPTH. The PTH-derivatives were separated by reverse-phase HPLC over a BROWNLEE C-18 column (220 ×2.1 mm). The initial yield for the coupling step was calculated from the amount of PTH-derivatives present in the first cycle and by the amount of protein spotted. As a standard marker for amino acid sequence, the repetitive yield from myoglobin was determined from peak heights of valine, leucine, and glutamic acid according to the positions. The repetitive yield from β-lactoglobulin was calculated for leucine, isoleucine, and valine residues. The N-terminal amino acid sequence of SUAM was D D M T T A D Q S P K L Q G E E A (T/A) L (I/A) (V/K) (Seq. ID No. 12).

The above procedures were repeated and an identical amino acid sequence was obtained. A protein-nucleic acid TBLASTN search (NCBI) and Swissprot amino acid data bank search were used to align the SUAM-terminal amino acid sequence with previously sequenced genes and proteins. No similarities were found establishing that the bacterial SUAM protein is a novel protein.

EXAMPLE 8

Identification of Lactoferrin Binding Proteins in *Streptococcus Dysgalactiae* Subsp. *Dysgalactiae* and *Streptococcus Agalactiae* Isolated from Cows with Mastitis (Prior Art) (Described in Park, H. M., R. A. Almeida, and S. P. Oliver, FEMS Microbiol. Lett. 207:87 (2000))

This paper demonstrates the presence of lactoferrin-binding proteins in two major bovine mammary pathogens, *Streptococcus dysgalactiae* subsp. *dysgalactiae* (*S. dysgalactiae*) and *Streptococcus agalactiae.*

Three strains of *S. dysgalactiae* and five strains of *S. agalactiae* were used to identify lactoferrin-binding proteins (LBPs). LBPs from extracted surface proteins were detected by polyacrylamide gel electrophoresis and Western blotting. All strains of *S. dysgalactiae* evaluated had 52 kDa and 74 kDa protein bands. All strains of *S. agalactiae* evaluated had 52 kDa, 70 kDa and 110 kDa protein bands. In addition, a 45 kDa band was detected in two of five *S. agalactiae* strains evaluated. This study demonstrated that *S. dysgalactiae* and *S. agalactiae* of bovine origin contain at least two major LBP's. Thus, LBP's are present in several *Streptococcus* species that cause mastitis in dairy cows.

EXAMPLE 9

Binding of bovine lactoferrin to *Streptococcus dysgalactiae* subsp. *dysgalactiae* isolated form cows with mastitis (prior art) (Park, H. M., R. A. Almeida, D. A. Luther, and S. P. Oliver, FEMS Microbiol. Lett. 208:35 (2000))

Three strains of *S. dysgalactiae* subsp. *dysgalactiae* (one of which is strain ATCC 27957) were used to determine if bovine lactoferrin (LF) binds to bacterial cells by biotin avidin binding assay (BABA), enzyme-linked immunosorbent assay (ELISA), and binding inhibition assay. Binding assays revealed that all strains of *S. dysgalactiae* subsp. *dysgalactiae* (*S. dysgalactiae*) evaluated in this study bound to LF, although some differences in LF binding capability among strains and between methods used were detected. Binding of LF was not inhibited by transferrin (TF) and LF moiety molecules (mannose, galactose, and lactose) but by LF. This study demonstrates that *S. dysgalactiae* binds to bovine LF in a specific manner.

EXAMPLE 10

Production of Antibodies Against SUAM (Whole Protein) and to a Synthetic Peptide (pepSUAM) Encompassing 15 Amino Acids Near the N-Terminus of SUAM SUAM antibodies were needed to test the biological role of SUAM on adherence to and internalization of *S. uberis* into bovine mammary epithelial cells, and to test protective effects of SUAM antibody on these in vitro approaches. To obtain antibodies, purified SUAM as described in Example 6 was sent to Quality Bioresources Inc. (QBI, Seguin, Tex.) for custom antibody production. For production of antibodies against SUAM, ~300 µg of purified protein was used to immunize two rabbits. For production of antibodies against SUAM-derived peptide (pepSUAM), Bethyl Laboratories, Inc. (Montgomery, Tex.) synthesized the selected peptide based on the N-terminal amino acid sequence M T T A D Q S P K L Q G E E A (Seq. ID No. 4). All peptides were HPLC purified and conjugated to KLH for immunization. PepSUAM induced a high immune response with production of immunologic response which yielded 20 mg of affinity purified antibody.

EXAMPLE 11

Cross-Reactivity of pepSUAM and SUAM Antibodies with Several Strains of *S. Uberis*.

To ensure that SUAM is not a rare protein found only in one strain of *S. uberis*, and that research or prophylactic products developed will have broad significance, several strains of *S. uberis* from diverse locations were tested by Western blotting. Strains evaluated were from Tennssee, Colorado, Washington and New Zealand. The different *S. uberis* strains were cultured overnight in Todd Hewitt broth and surface proteins were extracted in Laemmli sample buffer. SDS-PAGE polyacrylamide gels (7.5%) were electrophoresed followed by transfer to nitrocellulose membranes. They were blocked in PBSTG (phosphate buffered saline, 0.05% (v/v) TWEEN-20, and 0.1% (w/v) porcine gelatin) for 1 h. Affinity purified rabbit anti-pepSUAM and rabbit anti-SUAM antibodies were diluted in PBSTG (1:2000) and blots treated for 1.5 h. Following washing of blots with several changes of PBST, a 1:2000 dilution in PBSTG of peroxidase-conjugated affipure F(ab')2 fragment donkey anti-rabbit IgG (H+L) was applied. The SUAM protein band was revealed with the peroxidase substrate 4 CN (4-chloro-1-naphthol). The presence of a single dominant band on a blot of total *S. uberis* detergent extracted surface proteins attests to the specificity of the antibodies. The 112 kDa SUAM protein band is clearly visible. These results establish that SUAM is a ubiquitous protein in *S. uberis* strains and that pepSUAM may play a role as a universal immunogen to protect against *S. uberis* mastitis.

EXAMPLE 12

Cross-Reactivity of pepSUAM and SUAM Antibodies with *S. Agalactiae, S. Dysgalactiae* Subsp. *Dysgalactiae*, and *Streptococcus Pyogenes*.

Cross-reactivity of rabbit anti-SUAM whole protein antibodies and rabbit anti-pepSUAM antibodies between different *Streptococcus* species was investigated. Strains of *S. dysgalactiae* subsp. *dysgalactiae, S agalactiae* (from animals and humans), and *Streptococcus pyogenes* were cultured overnight in Todd Hewitt broth and bacterial surface proteins were extracted in Laemmli sample buffer. SDS-PAGE polyacrylamide gels (7.5%) were electrophoresed followed by transfer to nitrocellulose membranes. They were blocked in PBSTG (phosphate buffered saline. 0.05% (v/v) TWEEN-20, and 0.1% (w/v) porcine gelatin) for 1 h. Affinity purified rabbit anti-pepSUAM and rabbit anti-SUAM antibodies were diluted in PBSTG (1:2000) and blots treated for 1.5 h. The next treatment after washing blots with several changes of PBST was a 1:2000 dilution in PBSTG of peroxidase-conjugated affipure F (ab') 2 fragment donkey anti-rabbit IgG (H+L). The SUAM protein band was revealed with the peroxidase substrate 4CN (4-chloro-1-naphthol ). Western blot results showed cross reaction of pepSUAM and SUAM antibodies with proteins of other *Streptococcus* species, including the human pathogen *S. pyogenes*. The cross reaction with other proteins or protein fragments indicates that SUAM and its functions are conserved or partially conserved between *Streptococcus* species and that a vaccine based upon SUAM would have broad application.

EXAMPLE 13

Inhibitory Effect of SUAM and pepSUAM Antibodies on Adherence and Internalization of *S. uberis* to Bovine Mammary Epithelial Cells Two strains of *S. uberis* isolated from cows with clinical mastitis were incubated with increasing concentrations of SUAM and pepSUAM antibodies, co-cultured with bovine mammary epithelial cells and adherence of *S. uberis* to and internalization of *S. uberis* into mammary epithelial cells measured.

A bovine mammary epithelial cell line (MAC-T) was used. MAC-T cells were cultured in cell growth medium (CGM) in 24-well plates and incubated in 5% $CO_2$/balance air at 37° C. Monolayers were checked daily for confluence.

Two *S. uberis* strains isolated from cows with mastitis were used. For adherence and internalization assays, bacteria stored at −70° C. were thawed in a 37° C. water bath, streaked onto blood agar plates, and incubated for 16 h at 37° C. Bacteria were then inoculated into Todd-Hewitt broth (THB, Difco, Detroit, Mich.) for 2 h at 37° C. Bacterial suspensions were diluted in CGM to a concentration of $10^7$ bacteria per ml.

Each of the two strains of *S. uberis* was preincubated with several dilutions of SUAM and pepSUAM antibodies for 1 h at 37° C. After incubation, bacterial suspensions were washed three times to remove unbound antibodies and co-cultured with MAC-T cells for 2 h at 37° C. in 5% CO2: 95% air (vol/vol). In order to enumerate bacteria associated with MAC-T cells (adherent+internalized bacteria), MAC-T cells were washed 3 times to remove unbound bacteria and lysed with trypsin and triton. MAC-T cell lysates were 10-fold serially diluted, seeded in triplicate on blood agar plates, and incubated overnight at 37° C. After incubation, individual colonies were counted and expressed as colony forming units per ml (CFU/ml) of *S. uberis*.

In order to discriminate between *S. uberis* that adhered to the MAC-T cell surface from those that were internalized into MAC-T cells, an internalization assay was performed in parallel wells and under the same culture conditions as described for the adherence assay. The internalization assay was similar to the adherence assay with the exception that an antibiotic treatment directed to destroy bacteria that were not internalized was performed before lysing MAC-T cells. Following this, MAC-T cells were washed extensively, lysed as described before, and bacteria that were internalized were enumerated as described for the adherence assay. The number of adherent bacteria was calculated by subtracting the number of internalized bacteria from MAC-T cell-associated bacteria.

Pretreatment with SUAM (FIGS. 1 A&B) or pepSUAM (FIGS. 1 C&D) antibodies reduced adherence and internalization of *S. uberis* to mammary epithelial cells. The greatest adherence and internalization of *S. uberis* was observed when S. uberis was not pretreated with SUAM or pepSUAM antibodies. The lowest adherence and internalization of S. uberis was detected when higher concentrations of antibodies were used. FIG. 1 A-D show a dilution effect on adherence and internalization, which confirms the inhibitory effect of SUAM and pepSUAM antibodies on adherence to and internalization of S. uberis into MAC-T cells. Results from this experiment showed the inhibitory effect of SUAM and pepSUAM antibodies on adherence and internalization of S. uberis into MAC-T cells and indicate the value of SUAM and pepSUAM as immunogens for controlling this economically important disease of dairy cows.

EXAMPLE 14

Theoretical Elucidation of SUAM DNA Sequence and Confirmation by PCR and Restriction Digest Theoretical elucidation of the DNA sequence from the pepSUAM amino acid sequence permitted DNA synthesis of the SUAM gene using PCR techniques. The pepSUAM amino acid sequence (MTTADQSPKLQGEEA) (Seq. ID No. 4) was used to search a S. uberis genomic database (Wellcome Trust Sanger Institute) to identify a single fragment of the genome, also known as "contig", that matched the DNA sequence of pepSUAM amino acids. The match for pepSUAM was 100% for this DNA contig and this was the only match of this quality in the entire existing S. uberis genomic database. From this DNA contig, several PCR primers were designed and used in PCR reactions to obtain a unique DNA fragment. Subsequent analysis of this PCR fragment showed physical and DNA sequence characteristics similar to that of the elucidated SUAM gene. These results indicate that a unique and single gene of the S. uberis genomic sequence is responsible for coding SUAM and that we generated unique PCR primers and defined PCR conditions for the synthesis of SUAM.

Using the ExPASy Home Page Translate Tool (Swiss Institute of Bioinformatics), the S. uberis genomic contig DNA sequence was translated to amino acid sequences, in all possible reading frames. Only one of the six possible translations contained an open reading frame (an area without stop codons) long enough to code for the S. uberis protein. This sequence was checked using a BLAST search against the entire National Center for Biotechnology Information (NCBI) genomic database and appears to be unique, with only partial segments showing homology.

The sequence shown in FIG. 3 is the hypothetical SUAM gene sequence with some additional sequence included before and after, 3,041 nucleotides. This sequence is designated as Seq. ID No. 1. The coding region for the N-terminal sequence begins at nucleotide 311 and ends at 376 (underlined). The coding region for the peptide used to generate antibody is from nucleotide 317 to 360 (bold). The open reading frame, i.e. gene, ends at the stop/termination codon represented by TAA, nucleotides 2837 to 2839.

FIG. 4 shows the translation of the nucleotide sequence of Seq. ID No. 1 in the correct reading frame. This amino acid sequence is designated Seq. ID No. 2. The N-terminal sequence segment is underlined and the peptide used to generate the antibody to pepSUAM is underlined and bold. The end that corresponds to the above sequence (bold TAA in FIG. 3) is marked by the dash following the bold GKK, which would be coded for by GGCAAAAAA.

This selected coding region was used to design primers for its amplification by PCR. Three separate pairs of primers that bound to six individual sites were designed to generate three slightly different fragments from this same gene. These primers successfully generated PCR products of the predicted length. This provides very strong evidence that this gene is present in the strain of S. uberis (S. uberis UT888) from which the S. uberis protein (SUAM) was purified and the N-terminal peptide sequence was determined. One of these primers was homologous to the coding region for the N-terminal sequence providing further support that the correct gene was amplified.

In an effort to determine additional amino acid/protein and nucleic acid/DNA sequence, three independent pairs of PCR primers were designed from the S. uberis genomic database sequence, contig sub114a06.

TABLE 1

Name, nucleotide composition and expected PCR product size.

| NAME | PRIMER | SEQ ID NO. | PRODUCT SIZE |
|---|---|---|---|
| LFbpDL5forward | 5'-GTC ATT TGG TAG GAG TGG CTG-3' | 6 | 2,970 bp |
| LFbpDL6reverse | 5'-TGG TTG ATA TAG CAC TTG GTG AC-3' | 7 | 2,970 bp |
| LFbpDL7forward | *5'-GGA TGA CAT GAC AAC TGC TGA TC-3' | 8 | 2,639 bp |
| LFbpDL8reverse | 5'-CAA TTG TCA GCA CGT CTC TGT AC-3' | 9 | 2,639 bp |
| LFbpDL9forward | 5'-CTT GGA ACT GGT GTT GGT ATG G-3' | 10 | 2,561 bp |
| LFbpDL10reverse | 5'-CAG GTG TTA CTT CAG GTG CTA C-3' | 11 | 2,561 bp |

*pepSUAM coding region.

PCR reaction was run using an iCycler (BioRad) and conditions used were:
Cycle 1: (1×) Step 1: 95° C. for 2 min
Cycle 2: (30×) Step 1: 94° C. for 30 sec
　Step 2: 94° C. for 30 sec
　Step 3: 68° C. for 3 min
Cycle 3: (1×) Step 7: 68° C. for 7 min
Cycle 4: (1×) Step 7: 4° C. holding Reactions components used were as follows:
Primer forward: 0.5 µM
Primer reverse: 0.5 µM
Genomic DNA template: 0.5 µg
dNTP's: 200 µM each
$MgCl_2$: 1.5 mM Taq polymerase: 0.825 U PCR fragments obtained corresponded to the expected theoretical product size (Table 1). These results indicate that the PCR fragments obtained show a high degree of similarity with the theoretical SUAM gene. Further confirmation was done to compare the restriction enzyme map of the PCR fragments with the corresponding theoretical SUAM sequence.

Restriction Digest Confirmation: The longest PCR product of 2,970 bp, which includes a start and stop codon and therefore represents the entire gene, was further processed to confirm the specificity of the PCR reaction and further characterize the S. uberis SUAM gene. Restriction enzyme digestion cuts DNA at specific locations that are recognized by the different enzymes based upon their nucleotide sequence. The entire gene sequence was analyzed using NEBcutter at the New England BioLabs web site. Three restriction enzymes, Bcl I, Hpa I, and Nla III were chosen based on their ability to recognize specific sequence sites that when cut would generate distinctly identifiable fragments.

TABLE 2

Restriction enzymes, site of digestion (coordinates) and expected length of digested DNA.

| Enzyme | Coordinates (bp #) | Length (bp) |
|---|---|---|
| Bcl I | 329-2632 | 2304 |
| Bcl I | 2633-3041 | 409 |
| Bcl I | 1-328 | 328 |
| Hpa I | 1625-3041 | 1417 |
| Hpa I | 1-1204 | 1204 |
| Hpa I | 1205-1624 | 420 |
| Nla III | 1580-3041 | 1462 |
| Nla III | 320-1367 | 1048 |
| Nla III | 1-319 | 319 |
| Nla III | 1368-1579 | 212 |

Digestion of the 2,970 bp PCR fragment generated the expected patterns (lower molecular weight products were not clearly detected due to detection limits, as would be expected). The combined results of six primer binding sites and 10 restriction cut sites by 3 enzymes confirmed that PCR fragments have a restriction pattern similar to that of the theoretical SUAM sequence (FIG. 3, Seq. ID No. 1). These results, together with those from PCR reactions using several primer combinations, indicate that the PCR generated DNA fragment is similar to the theoretical SUAM nucleic acid sequence.

EXAMPLE 15

DNA Sequencing of SUAM

The SUAM gene was amplified, cloned and sequenced from the mastitis pathogen S. uberis strain UT 888. The results of this sequencing were that S. uberis SUAM has 99% sequence identity to the theoretical SUAM gene identified in the Sanger S. uberis genomic database by homology to the reverse translated peptide sequence described in Example 14.

The 2,970 bp PCR amplicon encompassing the SUAM gene was generated with primers LFbpDL5forward and LFbpDL6reverse shown in Table 1 in Example 14 (Seq ID Nos. 6 & 7). The product was gel purified from a 1.2% SeaPlaque GTG agarose gel (BioWhittaker Molecular Applications, Rockland, Me.) with the QIAEX II gel extraction kit (Qiagen Inc., Valencia, Calif.). The cloning into plasmid pCR-XL-TOPO of the purified amplicon was by the interaction of nontemplate-dependent polymerase generated adenine (A), overhangs of the amplicon and thymine (T), and overhangs of the vector. A mixture of recombinant Taq polymerase and Pyrococus DNA polymerase was used to minimize polymerase reading error (Invitrogen, Carlsbad, Calif.). Chemically competent Escherichia coli, TOP 10 cells, were transformed and selected on Luria-Bertani agar with 50 μg/ml kanamycin (Invitrogen, Carlsbad, Calif.). The positive clone was confirmed by isolation of the plasmid, (Wizard Plus SV miniprep DNA purification system; Promega, Madison, Wis.), re-amplification of the insert, and digestion with restriction enzymes (New England BioLabs, Inc., Beverly, Mass.) based upon restriction sites picked from the theoretical sequence.

Confirmation of the theoretical sequence (The Wellcome Trust Sanger Institute, Hinxton, Cambs, UK) and determination of the actual sequence from S. uberis 888 was accomplished by automated DNA sequencing (Molecular Biology Resource Facility, The University of Tennessee, Knoxville, Tenn.) of the plasmid in the region of insertion in both a forward and reverse direction to sequence both strands. The first primers were of known sites on the plasmid; M13 forward and M13 reverse, with subsequent primers (Integrated DNA Technologies, Coralville, Iowa) being chosen from the 3' end of the determined nucleic acid code. Four rounds of sequencing yielded enough DNA sequence code to transverse the insert in each direction. Sequence contig assembly was performed with the aid of the software Sequencher ver. 4.0.2 (Gene Codes Corporation, Ann Arbor, Mich.).

As each forward and reverse contig was assembled, the overlapping regions provided a quality control check for sequencing error. When the forward and the reverse assembled contigs were compared, this provided an additional quality control check. There were at least two and often more sequencing reactions used for each position in the final nucleic acid sequence. Final comparison and confirmation of the theoretical database sequence, and actual S. uberis UT 888 sequence were made with BLAST 2 SEQUENCES, BLASTN ver. 2.2.5 (National Center for Biotechnology Information, Bethesda, Md.). Results of this alignment were: Identities=2948 (theoretical)/2970 (actual) or 99% similarity.

The complete SUAM DNA sequence is presented in FIG. 5 and is designated Seq. ID No. 5. The complete SUAM gene DNA sequence did not show homology with other S. uberis genes reported in the Sanger S. uberis genomic database. This indicates that the SUAM gene codes for a unique S. uberis protein.

The amino acid sequence encoded by the SUAM DNA sequence of Seq. ID No. 5 is presented in FIG. 6. Polypeptide fragments encoded by the DNA Sequence of Seq. ID No. 5 are shown in Seq. ID Nos. 13 to 17, respectively, in order of appearance in FIG. 6. In FIG. 6, the presence of three sequential asterisks (***) indicates the position of a stop codon in the nucleotide sequence of Seq. ID No. 5. The underlined portion of amino acid sequence of FIG. 6 represents the N-terminal sequence of the SUAM protein. The underlined and bold portion of the sequence of FIG. 6 represents pepSUAM.

The SUAM polypeptide is shown in Seq. ID No. 15, preferably from amino acids 64 to 905 and most preferably from amino acids 66 to 905. The pepSUAM polypeptide is shown in Seq. ID No. 15 at amino acids 66 to 80.

The terms and expressions which have been employed in the foregoing specification are used as terms of description and not limitation, and there is no intention that the use of such terms and expressions excludes equivalents of the features shown and described above. Further modifications, uses, and applications of the invention described herein will be apparent to those skilled in the art. It is intended that such modifications be encompassed in the following claims.

The invention claimed is:

1. An isolated nucleic acid that encodes a polypeptide comprising the amino acid sequence of SEQ ID NO: 4.

2. The isolated nucleic acid of claim 1 that encodes a polypeptide comprising the amino acid sequence of SEQ ID NO: 2 or SEQ ID NO: 15.

3. The isolated nucleic acid of claim 1 that comprises the nucleotide sequence of SEQ ID NO: 5.

4. The isolated nucleic acid of claim 3 that comprises the sequence of nucleotides 317 to 2836 of SEQ ID NO: 1 or the sequence of nucleotides 289 to 2808 of SEQ ID NO: 3.

* * * * *